US006410707B2

(12) United States Patent
Wagner et al.

(10) Patent No.: US 6,410,707 B2
(45) Date of Patent: Jun. 25, 2002

(54) RECOMBINANT PREPARATION OF CALCITONIN FRAGMENTS AND USE THEREOF IN THE PREPARATION OF CALCITONIN AND RELATED ANALOGS

(75) Inventors: Fred W. Wagner, Walton; Jay S. Stout, Lincoln; Dennis B. Henriksen, Lincoln; Bruce E. Partridge, Lincoln; Bart Holmquist, Lincoln; Julie A. Frank, Lincoln, all of NE (US)

(73) Assignee: BioNebraska, Inc., Lincoln, NE (US)

( * ) Notice: Subject to any disclaimer, the term of this patent is extended or adjusted under 35 U.S.C. 154(b) by 108 days.

(21) Appl. No.: 09/750,913

(22) Filed: Jan. 2, 2001

Related U.S. Application Data

(62) Division of application No. 09/139,819, filed on Aug. 25, 1998, now Pat. No. 6,251,635, which is a division of application No. 08/595,868, filed on Feb. 6, 1996, now Pat. No. 5,962,270.

(51) Int. Cl.[7] .......................... C07H 21/04; C12N 1/20; C12N 15/00; A61K 38/00; C12P 21/04
(52) U.S. Cl. ................ 536/23.2; 435/252.3; 435/320.1; 435/69.1; 435/69.7; 536/23.1; 536/23.4; 530/300; 530/307; 530/325; 530/350
(58) Field of Search ............................ 435/69.7, 252.3, 435/320.1, 69.1; 530/300, 350, 307; 536/23.1, 23.2, 23.4

(56) References Cited

U.S. PATENT DOCUMENTS

| 3,798,203 A | 3/1974 | Brugger et al. ............. 530/307 |
| 3,891,614 A | 6/1975 | Sakakibara et al. ......... 530/307 |
| 4,086,221 A | 4/1978 | Sakakibara et al. ......... 530/307 |
| 4,401,593 A | 8/1983 | Orlowski et al. ............ 530/307 |
| 4,644,054 A | 2/1987 | Kempe ....................... 530/307 |
| 4,658,014 A | 4/1987 | Kempe ....................... 530/307 |
| 4,659,804 A | 4/1987 | Orlowski et al. ............ 530/307 |
| 4,743,677 A | 5/1988 | Noda et al. .................. 530/307 |
| 4,804,742 A | 2/1989 | Neiss et al. .................. 530/307 |
| 5,013,653 A | 5/1991 | Huston et al. .............. 435/69.7 |
| 5,093,241 A | 3/1992 | Bennett et al. ............. 435/69.4 |
| 5,143,844 A | 9/1992 | Abrahmsen et al. ..... 435/252.3 |
| 5,196,316 A | 3/1993 | Iwasai et al. ............... 435/69.1 |
| 5,332,664 A | 7/1994 | Craig et al. ................. 435/69.4 |
| 5,428,129 A | 6/1995 | Ohsaki et al. .............. 530/307 |
| 5,440,012 A | 8/1995 | Takei et al. ................. 530/307 |
| 5,527,881 A | 6/1996 | Poblet et al. ............... 530/307 |
| 5,595,887 A | 1/1997 | Coolidge et al. .......... 435/69.7 |
| 5,656,456 A | 8/1997 | Stout et al. ................. 435/69.4 |

FOREIGN PATENT DOCUMENTS

| CA | 1273750 | 9/1990 |
| EP | 191869 | 8/1986 |
| EP | 618219 | 10/1994 |
| GB | 1590645 | 6/1981 |
| JP | 02/219589 | 9/1990 |
| JP | 04/059795 | 2/1992 |
| JP | 05/140199 | 6/1993 |
| JP | 05/247087 | 9/1993 |
| JP | 05/255391 | 10/1993 |
| JP | 06/157593 | 6/1994 |
| JP | 06/298798 | 10/1994 |
| WO | 83/04028 | 11/1983 |
| WO | WO 89/10934 | 11/1989 |
| WO | WO/07005 | 6/1990 |
| WO | WO 94/15962 | 7/1994 |
| WO | WO 95/18152 | 7/1995 |

OTHER PUBLICATIONS

Murakami et al. Genomics 1(2): 159–166 (1987).*

Alvarez–Morales, et al. "Activation of the *Bradyhizobium jacponicum* nifH and nifDK operons is dependent on promoter–upstream DNA sequences," Oxford University Press, Oxford, United Kingdom, *Nucleic Acids Research*, 14: 4207–4227, (1986).

Bagdasarian, et al. "A protein required for secretion of cholera toxin through the outer membrane of *Vibrio cholerae*," Elsevier Science BV, Amsterdam, Netherlands, *Gene*, 26: 273–282, (1983).

Barnes "PCR amplification of up to 35–kb DNA with high fidelity and high yield from λ bacteriophage templates," National Academy of Sciences USA, Washington, DC, Proceedings, 91: 2216–2220, (1994).

Bolivar, et al. "Construction and characterization of new cloning vehicles. II. A multipurpose cloning system," Elsevier Science BV, Amsterdam, Netherlands, *Gene*, 2: 95–113 (1977).

Bornstein "Structure of alpha–1–CB8, a large cyanogen bromide produced fragment from the alpha–1 chain of rat collagen. The nature of a hydroxylamine–sensitive bond and composition of tryptic peptides," American Chemical Society, Columbus OH, *Biochemistry*, 9:2408–2421 (1970).

Brewer, et al. "Amino acid sequence of bovine thyrocalcitonin," National Academy of Sciences USA, Washington, DC, Proceeds, 63: 940–947 (1969).

Craig, et al. "Partial nucleotide sequence of human calcitonin precursor mRNA identifies flanking cryptic peptides," Macmillan Magazines Ltd., London, United Kingdom, *Nature*, 295: 345–347 (1982).

(List continued on next page.)

*Primary Examiner*—Ponnathapu Achutamurthy
*Assistant Examiner*—Tekchand Saidha
(74) *Attorney, Agent, or Firm*—Foley & Lardner

(57) ABSTRACT

A process for the recombinant preparation of a calcitonin fragment and the use of the fragment in the preparation of calcitonin and related analogs is provided. The process includes recombinantly forming a fusion protein which includes the calcitonin fragment linked to a carbonic anhydrase. The recombinantly formed fusion protein is subsequently cleaved to produce a polypeptide which includes the calcitonin fragment. A method for producing a calcitonin carba analog which includes condensing a desaminononapeptide with the recombinantly formed calcitonin fragment is also provided.

2 Claims, 12 Drawing Sheets-

OTHER PUBLICATIONS

Cumaraswamy, et al. "Cloning of a cDNA encoding sheep calcitonin from a thyroid C–cell library," Elsevier Science BV, Amsterdam, Netherlands, *Gene*, 126: 269–273 (1993).

Davey, et al. "Trypsin–mediated semisynthesis of salmon calcitonin," Munksgaard, Belgium, *International Journal of Peptide and Protein Research*, 45: 380–385 (1995).

Dente, et al. "pEMBL: a new family of single stranded plasmids," Oxford University Press, Oxford, United Kingdom, *Nucleic Acids Research*, 11: 1645–1655 (1983).

Ditta, et al. "Broad host range DNA cloning system for gram–negative bacteria: construction of a gene bank of *Rhizobium melitoti*," National Academy of Science USA, Washington, DC, Proceeds, 77: 7347–7351 (1980).

Forsman, et al. "Production of Active Human Carbonic Anhydrase II in *E. Coli*," Munksgaard, Copenhagen, Denmark, *Acta Chemica Scandinavica*, B42: 314–318 (1988).

Furste, et al. "Molecular cloning of the plasmid RP4 primase region in a multi–range tacP expression vector," Elsevier Science BV, Amsterdam, Netherlands, *Gene*, 48: 119–131 (1986).

Greenstein, et al. "Chemical Procedures for Synthesis of Peptides," John Wiley & Sons, Inc., New York, NY, *Chemistry of the Amino Acids*, 2: 804ff and 1016ff (1961).

Gribskov, et al. "The codon preference plot: graphic of protein coding sequences and prediction of gene expression," Oxford University Press, Oxford, United Kingdom, *Nucleic Acids Research*, 12: 539–549 (1984).

Gubler, et al. "A simple and very efficient method for generating cDNA libraries," Elsevier Science BV, Amsterdam, Netherlands, *Gene*, 25: 263–269 (1983).

Hewett–Emmett "Structure and evolutionary origins of the carbonic anhydrase multigene family," Plenum Press, New York, NY, *The Carbonic Anhydrase: Cellular Physiology and Molecular Genetics*, Dodgson, et al. Editors, Chap. 2: 15–32 (1991).

Jewell, et al. "Enhancement of the catalytic properties of human carbonic anhydrase III by site–directed mutagenesis," American Chemical Society, Washington, DC, *Biochemistry*, 30: 1484–1490 (1991).

Keutmann, et al. "Chemistry and physiology of the calcitonins: some recent advances," William Heinemann Medical Brooks, Ltd., London, United Kingdom, Endocrinology 1971: Proceedings of the Third International Symposium, 316–323 (1971).

Koutz, et al. "Structural comparison of the *Pichia pastoris* alcohol oxidase genes," John Wiley & Sons, Inc., Journals, *Yeast*, 5: 167–177 (1989).

Kunkel "Rapid and efficient site–specific mutagenesis without phenotypic selection," National Academy of Sciences USA, Washington, DC, Proceeds, 82: 488–492 (1985).

Lasmoles, et al. "Elucidation of the nucleotide sequence of chicken calcitonin mRNA: direct evidence for the expression of a lower vertebrate calcitonin–like gene in man and rat," Oxford University Press, Oxford, United Kingdom, *The EMBO Journal*, 4: 2603–2607 (1985).

Long, et al. "Cloning of *Rhizobium melitoti* nodulation genes by direct complementation of Nod⁻ mutants," McMillan Journals Ltd., *Nature*, 298: 485–488 (1982).

Martial, et al. "Predicted structure of rabbit N–terminal, calcitonin and katacalcin peptides," Academic Press, Inc., San Diego, CA, *Biochemical and Biophysical Research Communications*, 171: 1111–1114 (1990).

Murakami, et al. "Cloning, expression, and sequence homologies of cDNA for human carbonic anyhydrase II," Academic Press, Inc., San Diego, CA, *Genomics*, 1: 159–166 (1987).

Nakai, et al. "The gene for human carbonic anyhydrase II (CA2) is located at chromosome 8q22," S. Karger AG, Basel, Switzerland, *Cytognetics Cell Genetics*, 44: 234–235 (1987).

Nelkin, et al. "Structure and expression of a gene encoding human calcitonin and calcitonin gene related peptide," *Biochemical and Biophysical Research Communications*, 123: 648–655 (1984).

Pridmore "New and versatile cloning vectors with kanamycin–resistance marker," Elsevier Science BV, Amsterdam, Netherlands, *Gene*, 56: 309–312 (1987).

Rosenberg, et al. "Vectors for selective expression of cloned DNAs by T7 RNA polymerase," Elsevier Science BV, Amsterdam, Netherlands, *Gene*, 56: 125–135 (1987).

Sharpe "Broad host range cloning vectors for gram–negative bacteria," Elsevier Science BV, Amsterdam, Netherlands, *Gene*, 29: 93–102 (1984).

Studier, et al. "Use of T7 RNA polymerase to direct expression of cloned genes," Academic Press, Inc., San Diego, CA, *Methods Enzymol.*, 185: 60–89 (1990).

Tajima, et al. "High–level synthesis in *Escherichia coli* of recombinant human calcitonin: collagenase cleavage of the fusion protein and peptiglycine α–amidation," Elsevier Science Publishers, Amsterdam, Netherlands, *Journal of Fermentation and Bioengineering*, 72: 362–367 (1991).

Tanhauser, et al. "A T7 expression vector optimized for site–directed mutagenesis using oligodeoxyribonucleotide cassettes," Elsevier Science BV, Amsterdam, Netherlands, *Gene*, 117: 113–117 (1992).

Van Heeke, et al. "Gene fusions with human carbonic anyhydrase II for efficient expression and rapid single–step recovery of recombinant proteins: expression of the *Escherichia coli* F1–ATPase epsilon subunit," Academic Press Inc., San Diego, CA, *Protein Expression and Purification*, 4: 265–275 (1993).

Van Heeke, et al. "Synthesis of recombinant peptides," Humana Press Inc., Totowa, NJ, *Methods in Molecular Biology*, 36: 245–260 (1994).

Venta, et al. "Structure and exon to protein domain relationships of the mouse carbonic anyhydrase II gene," The American Society of Biological Chemists, Inc., Bethesda, MD, *The Journal of Biological Chemistry*, 260: 12130–12135 (1985).

Venta, et al. "Comparison of the 5' regions of human and mouse carbionic anyhydrase II genes and identification of possible requlatory elements," Elsevier Science BV, Amsterdam, Netherlands, *Biochimica et Biophysica Acta*, 826: 195–201 (1985).

Venta, et al. "Polymorphic gene for human carbonic anyhydrase II: a molecular disease marker located on chromosome 8," National Academy of Sciences USA, Washington, DC, Proceeds, 80: 4437–4440 (1983).

Verpoorte, et al. "Esterase activities of human carbionic anyhydrases B and C," American Society for Biochemistry and Molecular Biology, Inc., Bethesda, MD, *Journal of Biological Chemistry*, 242: 4221–4229 (1967).

Wallace, et al. "Hybridization of synthetic oligodeoxyribonucleotides to phi chi 174 DNA: the effect of single base pair mismatch," Oxford University Press, Oxford, United Kingdom, *Nucleic Acids Research*, 6: 3543–3557 (1979).

Wallace, et al. "The use of synthetic oligonucleotides as hybridization probes. II. Hybridization of oligonucleotides of mixed sequence to rabbit beta–blobin DNA," Oxford University Press, Oxford, United Kingdom, *Nucleic Acids Research*, 9: 879–894 (1981).

Yanisch Perron, et al. "Improved M13 phage cloning vectors and host strains: nucleotide sequences of the M13mp18 and Puc19 vectors," Elsevier Science BV, Amsterdam, Netherlands, *Gene*, 33: 103–119 (1985).

* cited by examiner

```
                 9                 18                27                36                45               54
5' ATG TCC CAT CAC TGG GGG TAC GGC AAA CAC AAC GGA CCT GAG CAC TGG CAT AAG
   --- --- --- --- --- --- --- --- --- --- --- --- --- --- --- --- --- ---
   Met Ser His His Trp Gly Tyr Gly Lys His Asn Gly Pro Glu His Trp His Lys 63                72                81                90                99              108
   GAC TTC CCC ATT GCC AAG GGA GAG CGC CAG TCC CCT GTT GAC ATC GAC ACT CAT
   --- --- --- --- --- --- --- --- --- --- --- --- --- --- --- --- --- ---
   Asp Phe Pro Ile Ala Lys Gly Glu Arg Gln Ser Pro Val Asp Ile Asp Thr His 117               126               135               144               153              162
   ACA GCC AAG TAT GAC CCT TCC CTG AAG CCC CTG TCT GTT TCC TAT GAT CAA GCA
   --- --- --- --- --- --- --- --- --- --- --- --- --- --- --- --- --- ---
   Thr Ala Lys Tyr Asp Pro Ser Leu Lys Pro Leu Ser Val Ser Tyr Asp Gln Ala 171               180               189               198               207              216
   ACT TCC CTG AGG ATC CTC AAC AAT GGT CAT GCT TTC AAC GTG GAG TTT GAT GAC
   --- --- --- --- --- --- --- --- --- --- --- --- --- --- --- --- --- ---
   Thr Ser Leu Arg Ile Leu Asn Asn Gly His Ala Phe Asn Val Glu Phe Asp Asp 225               234               243               252               261              270
   TCT CAG GAC AAA GCA GTG CTC AAG GGA GGA CCC CTG GAT GGC ACT TAC AGA TTG
   --- --- --- --- --- --- --- --- --- --- --- --- --- --- --- --- --- ---
   Ser Gln Asp Lys Ala Val Leu Lys Gly Gly Pro Leu Asp Gly Thr Tyr Arg Leu 279               288               297               306               315              324
   ATT CAG TTT CAC TTT CAC TGG GGT TCA CTT GAT GGA CAA GGT TCA GAG CAT ACT
   --- --- --- --- --- --- --- --- --- --- --- --- --- --- --- --- --- ---
   Ile Gln Phe His Phe His Trp Gly Ser Leu Asp Gly Gln Gly Ser Glu His Thr 333               342               351               360               369              378
   GTG GAT AAA AAG AAA TAT GCT GCA GAA CTT CAC TTG GTT CAC TGG AAC ACC AAA
   --- --- --- --- --- --- --- --- --- --- --- --- --- --- --- --- --- ---
   Val Asp Lys Lys Lys Tyr Ala Ala Glu Leu His Leu Val His Trp Asn Thr Lys 387               396               405               414               423              432
   TAT GGG GAT TTT GGG AAA GCT GTG CAG CAA CCT GAT GGA CTG GCC GTT CTA GGT
   --- --- --- --- --- --- --- --- --- --- --- --- --- --- --- --- --- ---
   Tyr Gly Asp Phe Gly Lys Ala Val Gln Gln Pro Asp Gly Leu Ala Val Leu Gly 441               450               459               468               477              486
   ATT TTT TTG AAG GTT GGC AGC GCT AAA CCG GGC CTT CAG AAA GTT GTT GAT GTG
   --- --- --- --- --- --- --- --- --- --- --- --- --- --- --- --- --- ---
   Ile Phe Leu Lys Val Gly Ser Ala Lys Pro Gly Leu Gln Lys Val Val Asp Val
```

FIG. 6A

```
        495         504         513         522         531         540
CTG GAT TCC ATT AAA ACA AAG GGC AAG AGT GCT GAC TTC ACT AAC TTC GAT CCT
--- --- --- --- --- --- --- --- --- --- --- --- --- --- --- --- --- ---
Leu Asp Ser Ile Lys Thr Lys Gly Lys Ser Ala Asp Phe Thr Asn Phe Asp Pro 549         558         567         576         585         594
CGT GGC CTC CTT CCT GAA TCC TTG GAT TAC TGG ACC TAC CCA GGC TCA CTG ACC
--- --- --- --- --- --- --- --- --- --- --- --- --- --- --- --- --- ---
Arg Gly Leu Leu Pro Glu Ser Leu Asp Tyr Trp Thr Tyr Pro Gly Ser Leu Thr 603         612         621         630         639         648
ACC CCT CCT CTT CTG GAA TGT GTG ACC TGG ATT GTG CTC AAG GAA CCC ATC AGC
--- --- --- --- --- --- --- --- --- --- --- --- --- --- --- --- --- ---
Thr Pro Pro Leu Leu Glu Cys Val Thr Trp Ile Val Leu Lys Glu Pro Ile Ser 657         666         675         684         693         702
GTC AGC AGC GAG CAG GTG TTG AAA TTC CGT AAA CTT AAC TTC AAT GGG GAG GGT
--- --- --- --- --- --- --- --- --- --- --- --- --- --- --- --- --- ---
Val Ser Ser Glu Gln Val Leu Lys Phe Arg Lys Leu Asn Phe Asn Gly Glu Gly 711         720         729         738         747         756
GAA CCC GAA GAA CTG ATG GTG GAC AAC TGG CGC CCA GCT CAG CCA CTG AAG AAC
--- --- --- --- --- --- --- --- --- --- --- --- --- --- --- --- --- ---
Glu Pro Glu Glu Leu Met Val Asp Asn Trp Arg Pro Ala Gln Pro Leu Lys Asn 765         774         783         792         801         810
AGG CAA ATC AAA GCT TTC GTT GAC GAC GAC GAC AAC GGT AAA CTG TCT CAG GAG
--- --- --- --- --- --- --- --- --- --- --- --- --- --- --- --- --- ---
Arg Gln Ile Lys Ala Phe Val Asp Asp Asp Asp Asn Gly Lys Leu Ser Gln Glu 819         828         837         846         855         864
CTC CAT AAA CTG CAG ACT TAC CCG CGT ACT GAC GTT GGT GCT GGT ACC CCG GCT
--- --- --- --- --- --- --- --- --- --- --- --- --- --- --- --- --- ---
Leu His Lys Leu Gln Thr Tyr Pro Arg Thr Asp Val Gly Ala Gly Thr Pro Ala

TAA 3'
---
***
```

FIG. 6B

```
                              Gly  Lys  Lue  Ser  Gln  Glu  Lue  His
                              GGT  AAA  CTG  TCT  CAG  GAG  CTC  CAT

Lys  Lue  Gln  Thr  Tyr  Pro  Arg  Thr  Asp  Val  Gly  Ala  Gly  Thr
AAA  CTG  CAG  ACT  TAC  CCG  CGT  ACT  GAC  GTT  GGT  GCT  GGT  ACC

Pro
CCG
```

| SEQ ID NO: | SPECIES | 1 | | | | 5 | | | | | 10 | | | | | 15 | |
|---|---|---|---|---|---|---|---|---|---|---|---|---|---|---|---|---|---|
| 37 | Eel | Cys | Ser | Asn | Leu | Ser | Thr | Cys | Val | Leu | Gly | Lys | Leu | Ser | Gln | Glu | |
| 38 | Salmon I | Cys | Ser | Asn | Leu | Ser | Thr | Cys | Val | Leu | Gly | Lys | Leu | Ser | Gln | Glu | |
| 39 | Salmon II | Cys | Ser | Asn | Leu | Ser | Thr | Cys | Val | Leu | Gly | Lys | Leu | Ser | Gln | Asp | |
| 40 | Salmon III | | Cys | Ser | Asn | Leu | Ser | Thr | Cys | Met | Leu | Gly | Lys | Leu | Ser | Gln | Asp |
| 41 | Chicken | Cys | Ala | Ser | Leu | Ser | Thr | Cys | Val | Leu | Gly | Lys | Leu | Ser | Gln | Glu | |
| 42 | Human | Cys | Gly | Asn | Leu | Ser | Thr | Cys | Met | Leu | Gly | Thr | Tyr | Thr | Gln | Asp | |
| 43 | Rabbit | Cys | Gly | Asn | Leu | Ser | Thr | Cys | Met | Leu | Gly | Thr | Tyr | Thr | Gln | Asp | |
| 44 | Porcine | Cys | Ser | Asn | Leu | Ser | Thr | Cys | Val | Leu | Ser | Ala | Tyr | Trp | Arg | Asn | |
| 45 | Bovine | Cys | Ser | Asn | Leu | Ser | Thr | Cys | Val | Leu | Ser | Ala | Tyr | Trp | Lys | Asp | |
| 46 | Sheep | Cys | Ser | Asn | Leu | Ser | Thr | Cys | Val | Leu | Ser | Ala | Tyr | Trp | Lys | Asp | |

FIG. 9A

| SEQ ID NO: | SPECIES | 16 | | | | 20 | | | | | 25 | | | | | 30 | | | | |
|---|---|---|---|---|---|---|---|---|---|---|---|---|---|---|---|---|---|---|---|---|
| 37 | Eel | Leu | His | Lys | Leu | Gln | Thr | Tyr | Pro | Arg | Thr | Asp | Val | Gly | Ala | Gly | Thr | Pro-NH$_2$ | | |
| 38 | Salmon I | Leu | His | Lys | Leu | Gln | Thr | Tyr | Pro | Arg | Thr | Asn | Thr | Gly | Ser | Gly | Thr | Pro-NH$_2$ | | |
| 39 | Salmon II | Leu | His | Lys | Leu | Gln | Thr | Phe | Pro | Arg | Thr | Asn | Thr | Gly | Ala | Gly | Val | Pro-NH$_2$ | | |
| 40 | Salmon III | Leu | His | Lys | Leu | Gln | Thr | Phe | Pro | Arg | Thr | Asn | Thr | Gly | Ala | Gly | Val | Pro-NH$_2$ | | |
| 41 | Chicken | Leu | His | Lys | Leu | Gln | Thr | Tyr | Pro | Arg | Thr | Asp | Val | Gly | Ala | Gly | Thr | Pro-NH$_2$ | | |
| 42 | Human | Phe | Asn | Lys | Phe | His | Thr | Phe | Pro | Gln | Thr | Ala | Ile | Gly | Val | Gly | Ala | Pro-NH$_2$ | | |
| 43 | Rabbit | Leu | Asn | Lys | Phe | His | Thr | Phe | Pro | Gln | Thr | Asp | Ile | Gly | Val | Val | Ala | Pro-NH$_2$ | | |
| 44 | Porcine | Leu | Asn | Asn | Phe | His | Arg | Phe | Ser | Gly | Met | Gly | Phe | Gly | Pro | Glu | Thr | Pro-NH$_2$ | | |
| 45 | Bovine | Leu | Asn | Asn | Tyr | His | Arg | Phe | Ser | Gly | Met | Gly | Phe | Gly | Pro | Glu | Thr | Pro-NH$_2$ | | |
| 46 | Sheep | Leu | Asn | Asn | Tyr | His | Arg | Tyr | Ser | Gly | Met | Gly | Phe | Gly | Pro | Glu | Thr | Pro-NH$_2$ | | |

FIG. 9B

```
GGA TCC AAG CTT GTT AAC GGT AAA CTG TCT CAG GAG CTC CAT
CCT AGG TTC GAA CAA TTG CCA TTT GAC AGA GTC CTC GAG GTA
  Bam HI    HindIII    HpaI AAA CTG CAG ACT TAC CCG CGT ACT GAC GTT GGT GCT GGT ACC
TTT GAC GTC TGA ATG GGC GCA TGA CTG CAA CCA CGA CCA TGG CCG GCT TAA GAT ATC GAA TTC GTC GAC
GGC CGA ATT CTA TAG CTT AAG CAG CAG
              EcoRV    EcoRI    SalI
```

FIG. 10

EXT
2

5'
GAC GAC GAA TTC GAT ATC TTA AGC CGG GGT ACC AGC ACC
AAC GTC AG

FIG. 11

EXT
3

5'
<u>GGA TCC</u> <u>AAG CTT</u> <u>GTT AAC</u> GGT AAA CTG TCT CAG GAG CTC CAT

AAA CTG CAG ACT TAC CCG CGT ACT GAC GTT GGT GCT GGT

ACC

SEQUENCE LISTING (1) GENERAL INFORMATION:

(iii) NUMBER OF SEQUENCES: 51

(2) INFORMATION FOR SEQ ID NO: 1:

(i) SEQUENCE CHARACTERISTICS:
      (A) LENGTH: 24 amino acids
      (B) TYPE: amino acid
      (C) STRANDEDNESS: <Unknown>
      (D) TOPOLOGY: linear (ii) MOLECULE TYPE: peptide (ix) FEATURE:
      (A) NAME/KEY: Modified-site
      (B) LOCATION: 1
      (D) OTHER INFORMATION: /note= "Xaa is Gly or Ser"

(ix) FEATURE:
      (A) NAME/KEY: Modified-site
      (B) LOCATION: 2
      (D) OTHER INFORMATION: /note= "Xaa is Lys, Thr or Ala"

```
(ix) FEATURE:
    (A) NAME/KEY: Modified-site
    (B) LOCATION: 3
    (D) OTHER INFORMATION: /note= "Xaa is Leu or Tyr"

(ix) FEATURE:
    (A) NAME/KEY: Modified-site
    (B) LOCATION: 4
    (D) OTHER INFORMATION: /note= "Xaa is Ser, Thr or Trp"

(ix) FEATURE:
    (A) NAME/KEY: Modified-site
    (B) LOCATION: 5
    (D) OTHER INFORMATION: /note= "Xaa is Gln, Lys or Arg"

(ix) FEATURE:
    (A) NAME/KEY: Modified-site
    (B) LOCATION: 6
    (D) OTHER INFORMATION: /note= "Xaa is Glu, Asp or Asn"

(ix) FEATURE:
    (A) NAME/KEY: Modified-site
    (B) LOCATION: 7
    (D) OTHER INFORMATION: /note= "Xaa is Leu or Phe"

(ix) FEATURE:
    (A) NAME/KEY: Modified-site
    (B) LOCATION: 8
    (D) OTHER INFORMATION: /note= "Xaa is His or Asn"

(ix) FEATURE:
    (A) NAME/KEY: Modified-site
    (B) LOCATION: 9
    (D) OTHER INFORMATION: /note= "Xaa is Lys or Asn"

(ix) FEATURE:
    (A) NAME/KEY: Modified-site
    (B) LOCATION: 10
    (D) OTHER INFORMATION: /note= "Xaa is Leu, Tyr or Phe"

(ix) FEATURE:
    (A) NAME/KEY: Modified-site
    (B) LOCATION: 11
    (D) OTHER INFORMATION: /note= "Xaa is Gln or His"

(ix) FEATURE:
    (A) NAME/KEY: Modified-site
    (B) LOCATION: 12
    (D) OTHER INFORMATION: /note= "Xaa is Thr or Arg"

(ix) FEATURE:
    (A) NAME/KEY: Modified-site
    (B) LOCATION: 13
    (D) OTHER INFORMATION: /note= "Xaa is Tyr or Phe"

(ix) FEATURE:
    (A) NAME/KEY: Modified-site
    (B) LOCATION: 14
    (D) OTHER INFORMATION: /note= "Xaa is Pro or Ser"

(ix) FEATURE:
    (A) NAME/KEY: Modified-site
    (B) LOCATION: 15
    (D) OTHER INFORMATION: /note= "Xaa is Arg, Gly or Gln"

(ix) FEATURE:
    (A) NAME/KEY: Modified-site
    (B) LOCATION: 16
    (D) OTHER INFORMATION: /note= "Xaa is Thr or Met"

(ix) FEATURE:
    (A) NAME/KEY: Modified-site
    (B) LOCATION: 17
    (D) OTHER INFORMATION: /note= "Xaa is Asp, Ala, Gly or
        Asn"

(ix) FEATURE:
    (A) NAME/KEY: Modified-site
    (B) LOCATION: 18
```

(D) OTHER INFORMATION: /note= "Xaa is Val, Leu, Ile, Phe
                or Thr"

(ix) FEATURE:
            (A) NAME/KEY: Modified-site
            (B) LOCATION: 20
            (D) OTHER INFORMATION: /note= "Xaa is Ala, Val, Pro or
                Ser"

(ix) FEATURE:
            (A) NAME/KEY: Modified-site
            (B) LOCATION: 21
            (D) OTHER INFORMATION: /note= "Xaa is Gly, Val or Glu"

(ix) FEATURE:
            (A) NAME/KEY: Modified-site
            (B) LOCATION: 22
            (D) OTHER INFORMATION: /note= "Xaa is Thr, Val or Ala"

(ix) FEATURE:
            (A) NAME/KEY: Modified-site
            (B) LOCATION: 24
            (D) OTHER INFORMATION: /note= "Xaa is any amino acid"

(xi) SEQUENCE DESCRIPTION: SEQ ID NO: 1:

Xaa Xaa Xaa Xaa Xaa Xaa Xaa Xaa Xaa Xaa Xaa Xaa Xaa Xaa Xaa Xa
1               5                   10                  15

Xaa Xaa Gly Xaa Xaa Xaa Pro Xaa
            20

(2) INFORMATION FOR SEQ ID NO: 2:

(i) SEQUENCE CHARACTERISTICS:
            (A) LENGTH: 23 amino acids
            (B) TYPE: amino acid
            (C) STRANDEDNESS: <Unknown>
            (D) TOPOLOGY: linear (ii) MOLECULE TYPE: peptide (ix) FEATURE:
            (A) NAME/KEY: Modified-site
            (B) LOCATION: 1
            (D) OTHER INFORMATION: /note= "Xaa is Gly or Ser"

(ix) FEATURE:
            (A) NAME/KEY: Modified-site
            (B) LOCATION: 2
            (D) OTHER INFORMATION: /note= "Xaa is Lys, Thr or Ala"

(ix) FEATURE:
            (A) NAME/KEY: Modified-site
            (B) LOCATION: 3
            (D) OTHER INFORMATION: /note= "Xaa is Leu or Tyr"

(ix) FEATURE:
            (A) NAME/KEY: Modified-site
            (B) LOCATION: 4
            (D) OTHER INFORMATION: /note= "Xaa is Ser, Thr or Trp"

(ix) FEATURE:
            (A) NAME/KEY: Modified-site
            (B) LOCATION: 5
            (D) OTHER INFORMATION: /note= "Xaa is Gln, Lys or Arg"

(ix) FEATURE:
            (A) NAME/KEY: Modified-site
            (B) LOCATION: 6
            (D) OTHER INFORMATION: /note= "Xaa is Glu, Asp or Asn"

(ix) FEATURE:
            (A) NAME/KEY: Modified-site
            (B) LOCATION: 7
            (D) OTHER INFORMATION: /note= "Xaa is Leu or Phe"

```
       (ix) FEATURE:
             (A) NAME/KEY: Modified-site
             (B) LOCATION: 8
             (D) OTHER INFORMATION: /note= "Xaa is His or Asn"

(ix) FEATURE:
             (A) NAME/KEY: Modified-site
             (B) LOCATION: 9
             (D) OTHER INFORMATION: /note= "Xaa is Lys or Asn"

(ix) FEATURE:
             (A) NAME/KEY: Modified-site
             (B) LOCATION: 10
             (D) OTHER INFORMATION: /note= "Xaa is Leu, Tyr or Phe"

(ix) FEATURE:
             (A) NAME/KEY: Modified-site
             (B) LOCATION: 11
             (D) OTHER INFORMATION: /note= "Xaa is Gln or His"

(ix) FEATURE:
             (A) NAME/KEY: Modified-site
             (B) LOCATION: 12
             (D) OTHER INFORMATION: /note= "Xaa is Thr or Arg"

(ix) FEATURE:
             (A) NAME/KEY: Modified-site
             (B) LOCATION: 13
             (D) OTHER INFORMATION: /note= "Xaa is Tyr or Phe"

(ix) FEATURE:
             (A) NAME/KEY: Modified-site
             (B) LOCATION: 14
             (D) OTHER INFORMATION: /note= "Xaa is Pro or Ser"

(ix) FEATURE:
             (A) NAME/KEY: Modified-site
             (B) LOCATION: 15
             (D) OTHER INFORMATION: /note= "Xaa is Arg, Gly or Gln"

(ix) FEATURE:
             (A) NAME/KEY: Modified-site
             (B) LOCATION: 16
             (D) OTHER INFORMATION: /note= "Xaa is Thr or Met"

(ix) FEATURE:
             (A) NAME/KEY: Modified-site
             (B) LOCATION: 17
             (D) OTHER INFORMATION: /note= "Xaa is Asp, Ala, Gly or
                  Asn"

(ix) FEATURE:
             (A) NAME/KEY: Modified-site
             (B) LOCATION: 18
             (D) OTHER INFORMATION: /note= "Xaa is Val, Leu, Ile, Phe
                  or Thr"

(ix) FEATURE:
             (A) NAME/KEY: Modified-site
             (B) LOCATION: 20
             (D) OTHER INFORMATION: /note= "Xaa is Ala, Val, Pro or
                  Ser"

(ix) FEATURE:
             (A) NAME/KEY: Modified-site
             (B) LOCATION: 21
             (D) OTHER INFORMATION: /note= "Xaa is Gly, Val or Glu"

(ix) FEATURE:
             (A) NAME/KEY: Modified-site
             (B) LOCATION: 22
             (D) OTHER INFORMATION: /note= "Xaa is Thr, Val or Ala"

(xi) SEQUENCE DESCRIPTION: SEQ ID NO: 2:

Xaa Xaa Xaa Xaa Xaa Xaa Xaa Xaa Xaa Xaa Xaa Xaa Xaa Xaa Xaa Xa
1               5                  10                 15
```

```
Xaa Xaa Gly Xaa Xaa Xaa Pro
            20
```

(2) INFORMATION FOR SEQ ID NO: 3:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is Gly, Ser or Ala"

(ix) FEATURE:
        (A) NAME/KEY: Modified-site
        (B) LOCATION: 2
        (D) OTHER INFORMATION: /note= "Xaa is Asn or Ser"

(ix) FEATURE:
        (A) NAME/KEY: Cleavage-site
        (B) LOCATION: 6
        (D) OTHER INFORMATION: /note= "Xaa is an aminosuberic acid
            linkage"

(ix) FEATURE:
        (A) NAME/KEY: Modified-site
        (B) LOCATION: 7
        (D) OTHER INFORMATION: /note= "Xaa is Val or Met"

(xi) SEQUENCE DESCRIPTION: SEQ ID NO: 3:

```
Xaa Xaa Leu Ser Thr Xaa Xaa Leu
1               5
```

(2) INFORMATION FOR SEQ ID NO: 4:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note= "Xaa is Gly, Ser or Ala"

(ix) FEATURE:
        (A) NAME/KEY: Modified-site
        (B) LOCATION: 2
        (D) OTHER INFORMATION: /note= "Xaa is Asn or Ser"

(ix) FEATURE:
        (A) NAME/KEY: Cleavage-site
        (B) LOCATION: 6
        (D) OTHER INFORMATION: /note= "Xaa is an aminosuberic acid
            linkage"

(ix) FEATURE:
        (A) NAME/KEY: Modified-site
        (B) LOCATION: 7
        (D) OTHER INFORMATION: /note= "Xaa is Val or Met"

(ix) FEATURE:
        (A) NAME/KEY: Modified-site
        (B) LOCATION: 9
        (D) OTHER INFORMATION: /note= "Xaa is Gly or Ser"

-continued

```
(ix) FEATURE:
    (A) NAME/KEY: Modified-site
    (B) LOCATION: 10
    (D) OTHER INFORMATION: /note= "Xaa is Lys, Thr or Ala"

(ix) FEATURE:
    (A) NAME/KEY: Modified-site
    (B) LOCATION: 11
    (D) OTHER INFORMATION: /note= "Xaa is Leu or Tyr"

(ix) FEATURE:
    (A) NAME/KEY: Modified-site
    (B) LOCATION: 12
    (D) OTHER INFORMATION: /note= "Xaa is Ser, Thr or Trp"

(ix) FEATURE:
    (A) NAME/KEY: Modified-site
    (B) LOCATION: 13
    (D) OTHER INFORMATION: /note= "Xaa is Gln, Lys or Arg"

(ix) FEATURE:
    (A) NAME/KEY: Modified-site
    (B) LOCATION: 14
    (D) OTHER INFORMATION: /note= "Xaa is Glu, Asp or Asn"

(ix) FEATURE:
    (A) NAME/KEY: Modified-site
    (B) LOCATION: 15
    (D) OTHER INFORMATION: /note= "Xaa is Leu or Phe"

(ix) FEATURE:
    (A) NAME/KEY: Modified-site
    (B) LOCATION: 16
    (D) OTHER INFORMATION: /note= "Xaa is His or Asn"

(ix) FEATURE:
    (A) NAME/KEY: Modified-site
    (B) LOCATION: 17
    (D) OTHER INFORMATION: /note= "Xaa is Lys or Asn"

(ix) FEATURE:
    (A) NAME/KEY: Modified-site
    (B) LOCATION: 18
    (D) OTHER INFORMATION: /note= "Xaa is Leu, Tyr or Phe"

(ix) FEATURE:
    (A) NAME/KEY: Modified-site
    (B) LOCATION: 19
    (D) OTHER INFORMATION: /note= "Xaa is Gln or His"

(ix) FEATURE:
    (A) NAME/KEY: Modified-site
    (B) LOCATION: 20
    (D) OTHER INFORMATION: /note= "Xaa is Thr or Arg"

(ix) FEATURE:
    (A) NAME/KEY: Modified-site
    (B) LOCATION: 21
    (D) OTHER INFORMATION: /note= "Xaa is Tyr or Phe"

(ix) FEATURE:
    (A) NAME/KEY: Modified-site
    (B) LOCATION: 22
    (D) OTHER INFORMATION: /note= "Xaa is Pro or Ser"

(ix) FEATURE:
    (A) NAME/KEY: Modified-site
    (B) LOCATION: 23
    (D) OTHER INFORMATION: /note= "Xaa is Arg, Gly or Gln"

(ix) FEATURE:
    (A) NAME/KEY: Modified-site
    (B) LOCATION: 24
    (D) OTHER INFORMATION: /note= "Xaa is Thr or Met"
```

(ix) FEATURE:
    (A) NAME/KEY: Modified-site
    (B) LOCATION: 25
    (D) OTHER INFORMATION: /note= "Xaa is Asp, Ala, Gly or Asn"

(ix) FEATURE:
    (A) NAME/KEY: Modified-site
    (B) LOCATION: 26
    (D) OTHER INFORMATION: /note= "Xaa is Val, Leu, Ile, Phe or Thr"

(ix) FEATURE:
    (A) NAME/KEY: Modified-site
    (B) LOCATION: 28
    (D) OTHER INFORMATION: /note= "Xaa is Ala, Val, Pro or Ser"

(ix) FEATURE:
    (A) NAME/KEY: Modified-site
    (B) LOCATION: 29
    (D) OTHER INFORMATION: /note= "Xaa is Gly, Val or Glu"

(ix) FEATURE:
    (A) NAME/KEY: Modified-site
    (B) LOCATION: 30
    (D) OTHER INFORMATION: /note= "Xaa is Thr, Val or Ala"

(ix) FEATURE:
    (A) NAME/KEY: Modified-site
    (B) LOCATION: 32
    (D) OTHER INFORMATION: /note= "Xaa is any amino acid"

(xi) SEQUENCE DESCRIPTION: SEQ ID NO: 4:

```
Xaa Xaa Leu Ser Thr Xaa Xaa Leu Xaa Xaa Xaa Xaa Xaa Xaa Xaa Xa
 1               5                  10                  15

Xaa Xaa Xaa Xaa Xaa Xaa Xaa Xaa Xaa Xaa Gly Xaa Xaa Xaa Pro Xa
            20                  25                  30
```

(2) INFORMATION FOR SEQ ID NO: 5:

(i) SEQUENCE CHARACTERISTICS:
        (A) LENGTH: 69 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 5:

```
GGTAAACTGT CTCAGGAGCT CCATAAACTG CAGACTTACC CGCGTACTGA CGTTGGTGCT      60

GGTACCCCG                                                              69
```

(2) INFORMATION FOR SEQ ID NO: 6:

(i) SEQUENCE CHARACTERISTICS:
        (A) LENGTH: 23 amino acids
        (B) TYPE: amino acid
        (D) TOPOLOGY: linear (ii) MOLECULE TYPE: protein (xi) SEQUENCE DESCRIPTION: SEQ ID NO: 6:

```
Gly Lys Leu Ser Gln Glu Leu His Lys Leu Gln Thr Tyr Pro Arg Thr
 1               5                  10                  15

Asp Val Gly Ala Gly Thr Pro
            20
```

(2) INFORMATION FOR SEQ ID NO: 7:

(i) SEQUENCE CHARACTERISTICS:
        (A) LENGTH: 8 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Cleavage-site
        (B) LOCATION: 6
        (D) OTHER INFORMATION: /note= "Xaa is an aminosuberic acid
           linkage"

(xi) SEQUENCE DESCRIPTION: SEQ ID NO: 7:

```
Ser Asn Leu Ser Thr Xaa Val Leu
1               5
```

(2) INFORMATION FOR SEQ ID NO: 8:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 8:

```
GACGACGAAT TCGATATCTT AAGCCGGGGT ACCAGCACCA ACGTCAG          47
```

(2) INFORMATION FOR SEQ ID NO: 9:

(i) SEQUENCE CHARACTERISTICS:
        (A) LENGTH: 84 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 9:

```
GGATCCAAGC TTGTTAACGG TAAACTGTCT CAGGAGCTCC ATAAACTGCA GACTTACCCG          60

CGTACTGACG TTGGTGCTGG TACC                                                84
```

(2) INFORMATION FOR SEQ ID NO: 10:

(i) SEQUENCE CHARACTERISTICS:
        (A) LENGTH: 111 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 10:

```
GGATCCAAGC TTGTTAACGG TAAACTGTCT CAGGAGCTCC ATAAACTGCA GACTTACCCG          60

CGTACTGACG TTGGTGCTGG TACCCCGGCT TAAGATATCG AATTCGTCGA C                 111
```

(2) INFORMATION FOR SEQ ID NO: 11:

(i) SEQUENCE CHARACTERISTICS:
        (A) LENGTH: 867 base pairs
        (B) TYPE: nucleic acid
        (C) STRANDEDNESS: single
        (D) TOPOLOGY: linear -continued (ii) MOLECULE TYPE: DNA (genomic)

(ix) FEATURE:
(A) NAME/KEY: CDS
(B) LOCATION: 1..864

(xi) SEQUENCE DESCRIPTION: SEQ ID NO: 11:

| | | | | | | | | | | | | | | | | |
|---|---|---|---|---|---|---|---|---|---|---|---|---|---|---|---|---|
| ATG | TCC | CAT | CAC | TGG | GGG | TAC | GGC | AAA | CAC | AAC | GGA | CCT | GAG | CAC | TGG | 48 |
| Met | Ser | His | His | Trp | Gly | Tyr | Gly | Lys | His | Asn | Gly | Pro | Glu | His | Trp | |
| 1 | | | | 5 | | | | | 10 | | | | | 15 | | |
| CAT | AAG | GAC | TTC | CCC | ATT | GCC | AAG | GGA | GAG | CGC | CAG | TCC | CCT | GTT | GAC | 96 |
| His | Lys | Asp | Phe | Pro | Ile | Ala | Lys | Gly | Glu | Arg | Gln | Ser | Pro | Val | Asp | |
| | | | 20 | | | | | 25 | | | | | 30 | | | |
| ATC | GAC | ACT | CAT | ACA | GCC | AAG | TAT | GAC | CCT | TCC | CTG | AAG | CCC | CTG | TCT | 144 |
| Ile | Asp | Thr | His | Thr | Ala | Lys | Tyr | Asp | Pro | Ser | Leu | Lys | Pro | Leu | Ser | |
| | | 35 | | | | | 40 | | | | | 45 | | | | |
| GTT | TCC | TAT | GAT | CAA | GCA | ACT | TCC | CTG | AGG | ATC | CTC | AAC | AAT | GGT | CAT | 192 |
| Val | Ser | Tyr | Asp | Gln | Ala | Thr | Ser | Leu | Arg | Ile | Leu | Asn | Asn | Gly | His | |
| | 50 | | | | | 55 | | | | | 60 | | | | | |
| GCT | TTC | AAC | GTG | GAG | TTT | GAT | GAC | TCT | CAG | GAC | AAA | GCA | GTG | CTC | AAG | 240 |
| Ala | Phe | Asn | Val | Glu | Phe | Asp | Asp | Ser | Gln | Asp | Lys | Ala | Val | Leu | Lys | |
| 65 | | | | | 70 | | | | | 75 | | | | | 80 | |
| GGA | GGA | CCC | CTG | GAT | GGC | ACT | TAC | AGA | TTG | ATT | CAG | TTT | CAC | TTT | CAC | 288 |
| Gly | Gly | Pro | Leu | Asp | Gly | Thr | Tyr | Arg | Leu | Ile | Gln | Phe | His | Phe | His | |
| | | | | 85 | | | | | 90 | | | | | 95 | | |
| TGG | GGT | TCA | CTT | GAT | GGA | CAA | GGT | TCA | GAG | CAT | ACT | GTG | GAT | AAA | AAG | 336 |
| Trp | Gly | Ser | Leu | Asp | Gly | Gln | Gly | Ser | Glu | His | Thr | Val | Asp | Lys | Lys | |
| | | | 100 | | | | | 105 | | | | | 110 | | | |
| AAA | TAT | GCT | GCA | GAA | CTT | CAC | TTG | GTT | CAC | TGG | AAC | ACC | AAA | TAT | GGG | 384 |
| Lys | Tyr | Ala | Ala | Glu | Leu | His | Leu | Val | His | Trp | Asn | Thr | Lys | Tyr | Gly | |
| | | 115 | | | | | 120 | | | | | 125 | | | | |
| GAT | TTT | GGG | AAA | GCT | GTG | CAG | CAA | CCT | GAT | GGA | CTG | GCC | GTT | CTA | GGT | 432 |
| Asp | Phe | Gly | Lys | Ala | Val | Gln | Gln | Pro | Asp | Gly | Leu | Ala | Val | Leu | Gly | |
| | 130 | | | | | 135 | | | | | 140 | | | | | |
| ATT | TTT | TTG | AAG | GTT | GGC | AGC | GCT | AAA | CCG | GGC | CTT | CAG | AAA | GTT | GTT | 480 |
| Ile | Phe | Leu | Lys | Val | Gly | Ser | Ala | Lys | Pro | Gly | Leu | Gln | Lys | Val | Val | |
| 145 | | | | | 150 | | | | | 155 | | | | | 160 | |
| GAT | GTG | CTG | GAT | TCC | ATT | AAA | ACA | AAG | GGC | AAG | AGT | GCT | GAC | TTC | ACT | 528 |
| Asp | Val | Leu | Asp | Ser | Ile | Lys | Thr | Lys | Gly | Lys | Ser | Ala | Asp | Phe | Thr | |
| | | | | 165 | | | | | 170 | | | | | 175 | | |
| AAC | TTC | GAT | CCT | CGT | GGC | CTC | CTT | CCT | GAA | TCC | TTG | GAT | TAC | TGG | ACC | 576 |
| Asn | Phe | Asp | Pro | Arg | Gly | Leu | Leu | Pro | Glu | Ser | Leu | Asp | Tyr | Trp | Thr | |
| | | | 180 | | | | | 185 | | | | | 190 | | | |
| TAC | CCA | GGC | TCA | CTG | ACC | ACC | CCT | CCT | CTT | CTG | GAA | TGT | GTG | ACC | TGG | 624 |
| Tyr | Pro | Gly | Ser | Leu | Thr | Thr | Pro | Pro | Leu | Leu | Glu | Cys | Val | Thr | Trp | |
| | | 195 | | | | | 200 | | | | | 205 | | | | |
| ATT | GTG | CTC | AAG | GAA | CCC | ATC | AGC | GTC | AGC | AGC | GAG | CAG | GTG | TTG | AAA | 672 |
| Ile | Val | Leu | Lys | Glu | Pro | Ile | Ser | Val | Ser | Ser | Glu | Gln | Val | Leu | Lys | |
| | 210 | | | | | 215 | | | | | 220 | | | | | |
| TTC | CGT | AAA | CTT | AAC | TTC | AAT | GGG | GAG | GGT | GAA | CCC | GAA | GAA | CTG | ATG | 720 |
| Phe | Arg | Lys | Leu | Asn | Phe | Asn | Gly | Glu | Gly | Glu | Pro | Glu | Glu | Leu | Met | |
| 225 | | | | | 230 | | | | | 235 | | | | | 240 | |
| GTG | GAC | AAC | TGG | CGC | CCA | GCT | CAG | CCA | CTG | AAG | AAC | AGG | CAA | ATC | AAA | 768 |
| Val | Asp | Asn | Trp | Arg | Pro | Ala | Gln | Pro | Leu | Lys | Asn | Arg | Gln | Ile | Lys | |
| | | | | 245 | | | | | 250 | | | | | 255 | | |
| GCT | TTC | GTT | GAC | GAC | GAC | GAC | AAC | GGT | AAA | CTG | TCT | CAG | GAG | CTC | CAT | 816 |
| Ala | Phe | Val | Asp | Asp | Asp | Asp | Asn | Gly | Lys | Leu | Ser | Gln | Glu | Leu | His | |
| | | | 260 | | | | | 265 | | | | | 270 | | | |

```
AAA CTG CAG ACT TAC CCG CGT ACT GAC GTT GGT GCT GGT ACC CCG GCT      864
Lys Leu Gln Thr Tyr Pro Arg Thr Asp Val Gly Ala Gly Thr Pro Ala
        275                 280                 285

TAA                                                                  867
```

(2) INFORMATION FOR SEQ ID NO: 12:

(i) SEQUENCE CHARACTERISTICS:
        (A) LENGTH: 288 amino acids
        (B) TYPE: amino acid
        (D) TOPOLOGY: linear (ii) MOLECULE TYPE: protein (xi) SEQUENCE DESCRIPTION: SEQ ID NO: 12:

```
Met Ser His His Trp Gly Tyr Gly Lys His Asn Gly Pro Glu His Trp
 1               5                  10                  15

His Lys Asp Phe Pro Ile Ala Lys Gly Glu Arg Gln Ser Pro Val Asp
            20                  25                  30

Ile Asp Thr His Thr Ala Lys Tyr Asp Pro Ser Leu Lys Pro Leu Ser
            35                  40                  45

Val Ser Tyr Asp Gln Ala Thr Ser Leu Arg Ile Leu Asn Asn Gly His
    50                  55                  60

Ala Phe Asn Val Glu Phe Asp Asp Ser Gln Asp Lys Ala Val Leu Lys
65                  70                  75                  80

Gly Gly Pro Leu Asp Gly Thr Tyr Arg Leu Ile Gln Phe His Phe His
                85                  90                  95

Trp Gly Ser Leu Asp Gly Gln Gly Ser Glu His Thr Val Asp Lys Lys
                100                 105                 110

Lys Tyr Ala Ala Glu Leu His Leu Val His Trp Asn Thr Lys Tyr Gly
            115                 120                 125

Asp Phe Gly Lys Ala Val Gln Gln Pro Asp Gly Leu Ala Val Leu Gly
        130                 135                 140

Ile Phe Leu Lys Val Gly Ser Ala Lys Pro Gly Leu Gln Lys Val Val
145                 150                 155                 160

Asp Val Leu Asp Ser Ile Lys Thr Lys Gly Lys Ser Ala Asp Phe Thr
                165                 170                 175

Asn Phe Asp Pro Arg Gly Leu Leu Pro Glu Ser Leu Asp Tyr Trp Thr
            180                 185                 190

Tyr Pro Gly Ser Leu Thr Thr Pro Pro Leu Leu Glu Cys Val Thr Trp
        195                 200                 205

Ile Val Leu Lys Glu Pro Ile Ser Val Ser Ser Glu Gln Val Leu Lys
        210                 215                 220

Phe Arg Lys Leu Asn Phe Asn Gly Glu Gly Glu Pro Glu Glu Leu Met
225                 230                 235                 240

Val Asp Asn Trp Arg Pro Ala Gln Pro Leu Lys Asn Arg Gln Ile Lys
                245                 250                 255

Ala Phe Val Asp Asp Asp Asn Gly Lys Leu Ser Gln Glu Leu His
            260                 265                 270

Lys Leu Gln Thr Tyr Pro Arg Thr Asp Val Gly Ala Gly Thr Pro Ala
        275                 280                 285
```

(2) INFORMATION FOR SEQ ID NO: 13:

(i) SEQUENCE CHARACTERISTICS:
        (A) LENGTH: 31 amino acids
        (B) TYPE: amino acid (C) STRANDEDNESS: <Unknown>
        (D) TOPOLOGY: linear (ii) MOLECULE TYPE: peptide (ix) FEATURE:
        (A) NAME/KEY: Cleavage-site
        (B) LOCATION: 6
        (D) OTHER INFORMATION: /note= "Xaa is an aminosuberic acid
            linkage"

(xi) SEQUENCE DESCRIPTION: SEQ ID NO: 13:

Ser Asn Leu Ser Thr Xaa Val Leu Gly Lys Leu Ser Gln Glu Leu Hi
1               5                   10                  15

Lys Leu Gln Thr Tyr Pro Arg Thr Asp Val Gly Ala Gly Thr Pro
            20                  25                  30

(2) INFORMATION FOR SEQ ID NO: 14:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 14:

Phe Val Asp Asp Asp Asp Asn
1               5

(2) INFORMATION FOR SEQ ID NO: 15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 15:

GACGACGACG ATAAA                                                    15

(2) INFORMATION FOR SEQ ID NO: 16:

(i) SEQUENCE CHARACTERISTICS:
        (A) LENGTH: 5 amino acids
        (B) TYPE: amino acid
        (D) TOPOLOGY: linear (ii) MOLECULE TYPE: protein (xi) SEQUENCE DESCRIPTION: SEQ ID NO: 16:

Asp Asp Asp Asp Lys
1               5

(2) INFORMATION FOR SEQ ID NO: 17:

(i) SEQUENCE CHARACTERISTICS:
        (A) LENGTH: 12 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 17:

ATTGAAGGAA GA                                                       12

(2) INFORMATION FOR SEQ ID NO: 18:

(i) SEQUENCE CHARACTERISTICS:
        (A) LENGTH: 4 amino acids
        (B) TYPE: amino acid
        (D) TOPOLOGY: linear (ii) MOLECULE TYPE: protein (xi) SEQUENCE DESCRIPTION: SEQ ID NO: 18:

Ile Glu Gly Arg
1

(2) INFORMATION FOR SEQ ID NO: 19:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 19:

CATCCTTTTC ATCTGCTGGT TTAT                                24

(2) INFORMATION FOR SEQ ID NO: 20:

(i) SEQUENCE CHARACTERISTICS:
        (A) LENGTH: 8 amino acids
        (B) TYPE: amino acid
        (D) TOPOLOGY: linear (ii) MOLECULE TYPE: protein (xi) SEQUENCE DESCRIPTION: SEQ ID NO: 20:

His Pro Phe His Leu Leu Val Tyr
1           5

(2) INFORMATION FOR SEQ ID NO: 21:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 21:

Asp Asn Trp Arg Pro Ala Gln Pro Leu Lys Asn Arg Glu Ile Lys Ala
1           5                  10              15

(2) INFORMATION FOR SEQ ID NO: 22:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 24
        (D) OTHER INFORMATION: /note= "Xaa is any amino acid"

(xi) SEQUENCE DESCRIPTION: SEQ ID NO: 22:

Gly Lys Leu Ser Gln Glu Leu His Lys Leu Gln Thr Tyr Pro Arg Thr
1               5                   10                  15

Asp Val Gly Ala Gly Thr Pro Xaa
            20

(2) INFORMATION FOR SEQ ID NO: 23:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 23:

Gly Lys Leu Ser Gln Glu Leu His Lys Leu Gln Thr Tyr Pro Arg Thr
1               5                   10                  15

Asp Val Gly Ala Gly Thr Pro Ala
            20

(2) INFORMATION FOR SEQ ID NO: 24:

(i) SEQUENCE CHARACTERISTICS:
        (A) LENGTH: 48 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 24:

Val Asp Asn Trp Arg Pro Ala Gln Pro Leu Lys Asn Arg Glu Ile Lys
1               5                   10                  15

Ala Phe Val Asp Asp Asp Asn Gly Lys Leu Ser Gln Glu Leu His
            20                  25                  30

Lys Leu Gln Thr Tyr Pro Arg Thr Asp Val Gly Ala Gly Thr Pro Ala
        35                  40                  45

(2) INFORMATION FOR SEQ ID NO: 25:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 25:

Val Asp Asn Trp Arg Pro Ala Gln Pro Leu Lys Asn Arg Glu Ile Lys
1               5                   10                  15

Ala (2) INFORMATION FOR SEQ ID NO: 26:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 26:

AGCTTTCGTT GACGACGACG ATATCTT                                    27

(2) INFORMATION FOR SEQ ID NO: 27:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 27:

AGCTAAGATA TCGTCGTCGT CAACGAA                                    27

(2) INFORMATION FOR SEQ ID NO: 28:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 24
        (D) OTHER INFORMATION: /note= "Xaa is any amino acid"

(xi) SEQUENCE DESCRIPTION: SEQ ID NO: 28:

Gly Lys Leu Ser Gln Glu Leu His Lys Leu Gln Thr Tyr Pro Arg Thr
1            5                    10                  15

Asp Val Gly Ala Gly Thr Pro Xaa
        20

(2) INFORMATION FOR SEQ ID NO: 29:

(i) SEQUENCE CHARACTERISTICS:
        (A) LENGTH: 23 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 29:

Gly Lys Leu Ser Gln Glu Leu His Lys Leu Gln Thr Tyr Pro Arg Thr
1            5                    10                  15

Asn Thr Gly Ser Gly Thr Pro
        20

(2) INFORMATION FOR SEQ ID NO: 30:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Cleavage-site
        (B) LOCATION: 6
        (D) OTHER INFORMATION: /note= "Xaa is an aminosuberic acid
            linkage"

```
    (ix) FEATURE:
         (A) NAME/KEY: Modified-site
         (B) LOCATION: 32
         (D) OTHER INFORMATION: /note= "Xaa is any amino acid"

(xi) SEQUENCE DESCRIPTION: SEQ ID NO: 30:

Ser Asn Leu Ser Thr Xaa Val Leu Gly Lys Leu Ser Gln Glu Leu His
1               5                   10                  15

Lys Leu Gln Thr Tyr Pro Arg Thr Asp Val Gly Ala Gly Thr Pro Xaa
            20                  25                  30

(2) INFORMATION FOR SEQ ID NO: 31:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (ix) FEATURE:
         (A) NAME/KEY: Cleavage-site
         (B) LOCATION: 6
         (D) OTHER INFORMATION: /note= "Xaa is an aminosuberic acid
             linkage"

(xi) SEQUENCE DESCRIPTION: SEQ ID NO: 31:

Ser Asn Leu Ser Thr Xaa Val Leu Gly Lys Leu Ser Gln Glu Leu His
1               5                   10                  15

Lys Leu Gln Thr Tyr Pro Arg Thr Asp Val Gly Ala Gly Thr Pro Ala
            20                  25                  30

(2) INFORMATION FOR SEQ ID NO: 32:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 32:

GGATCCAAGC TTGTTA                                                16

(2) INFORMATION FOR SEQ ID NO: 33:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 33:

GTCGACGAAT TCGATA                                                16

(2) INFORMATION FOR SEQ ID NO: 34:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (genomic)
```

(xi) SEQUENCE DESCRIPTION: SEQ ID NO: 34:

GGATCCAAGC TTGTTAACGG TAAACTGTCT CAGGAGCTCC ATAAACTG            48

(2) INFORMATION FOR SEQ ID NO: 35:

(i) SEQUENCE CHARACTERISTICS:
      (A) LENGTH: 47 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 35:

CTGACGTTGG TGCTGGTACC CCGGCTTAAG ATATCGAATT CGTCGAC             47

(2) INFORMATION FOR SEQ ID NO: 36:

(i) SEQUENCE CHARACTERISTICS:
      (A) LENGTH: 57 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO: 36:

GGTACCAGCA CCAACGTCAG TACGCGGGTA AGTCTGCAGT TTATGGAGCT CCTGAGA    57

(2) INFORMATION FOR SEQ ID NO: 37:

(i) SEQUENCE CHARACTERISTICS:
      (A) LENGTH: 32 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 37:

Cys Ser Asn Leu Ser Thr Cys Val Leu Gly Lys Leu Ser Gln Glu Leu
1               5                  10                  15

His Lys Leu Gln Thr Tyr Pro Arg Thr Asp Val Gly Ala Gly Thr Pro
                20                  25                  30

(2) INFORMATION FOR SEQ ID NO: 38:

(i) SEQUENCE CHARACTERISTICS:
      (A) LENGTH: 32 amino acids
      (B) TYPE: amino acid
      (C) STRANDEDNESS: <Unknown>
      (D) TOPOLOGY: linear (ii) MOLECULE TYPE: peptide (xi) SEQUENCE DESCRIPTION: SEQ ID NO: 38:

Cys Ser Asn Leu Ser Thr Cys Val Leu Gly Lys Leu Ser Gln Glu Leu
1               5                  10                  15

His Lys Leu Gln Thr Tyr Pro Arg Thr Asn Thr Gly Ser Gly Thr Pro
                20                  25                  30

(2) INFORMATION FOR SEQ ID NO: 39:

(i) SEQUENCE CHARACTERISTICS:
      (A) LENGTH: 32 amino acids
      (B) TYPE: amino acid (C) STRANDEDNESS: <Unknown>
            (D) TOPOLOGY: linear (ii) MOLECULE TYPE: peptide (xi) SEQUENCE DESCRIPTION: SEQ ID NO: 39:

Cys Ser Asn Leu Ser Thr Cys Val Leu Gly Lys Leu Ser Gln Asp Leu
1               5                   10                  15

His Lys Leu Gln Thr Phe Pro Arg Thr Asn Thr Gly Ala Gly Val Pro
            20                  25                  30

(2) INFORMATION FOR SEQ ID NO: 40:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 40:

Cys Ser Asn Leu Ser Thr Cys Met Leu Gly Lys Leu Ser Gln Asp Leu
1               5                   10                  15

His Lys Leu Gln Thr Phe Pro Arg Thr Asn Thr Gly Ala Gly Val Pro
            20                  25                  30

(2) INFORMATION FOR SEQ ID NO: 41:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 41:

Cys Ala Ser Leu Ser Thr Cys Val Leu Gly Lys Leu Ser Gln Glu Leu
1               5                   10                  15

His Lys Leu Gln Thr Tyr Pro Arg Thr Asp Val Gly Ala Gly Thr Pro
            20                  25                  30

(2) INFORMATION FOR SEQ ID NO: 42:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 42:

Cys Gly Asn Leu Ser Thr Cys Met Leu Gly Thr Tyr Thr Gln Asp Phe
1               5                   10                  15

Asn Lys Phe His Thr Phe Pro Gln Thr Ala Ile Gly Val Gly Ala Pro
            20                  25                  30

(2) INFORMATION FOR SEQ ID NO: 43:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 43:

Cys Gly Asn Leu Ser Thr Cys Met Leu Gly Thr Tyr Thr Gln Asp Leu
1               5                   10                  15

Asn Lys Phe His Thr Phe Pro Gln Thr Asp Ile Gly Val Val Ala Pro
            20                  25                  30

(2) INFORMATION FOR SEQ ID NO: 44:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 44:

Cys Ser Asn Leu Ser Thr Cys Val Leu Ser Ala Tyr Trp Arg Asn Leu
1               5                   10                  15

Asn Asn Phe His Arg Phe Ser Gly Met Gly Phe Gly Pro Glu Thr Pro
            20                  25                  30

(2) INFORMATION FOR SEQ ID NO: 45:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 45:

Cys Ser Asn Leu Ser Thr Cys Val Leu Ser Ala Tyr Trp Lys Asp Leu
1               5                   10                  15

Asn Asn Tyr His Arg Phe Ser Gly Met Gly Phe Gly Pro Glu Thr Pro
            20                  25                  30

(2) INFORMATION FOR SEQ ID NO: 46:

(i) SEQUENCE CHARACTERISTICS:
        (A) LENGTH: 32 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 46:

Cys Ser Asn Leu Ser Thr Cys Val Leu Ser Ala Tyr Trp Lys Asp Leu
1               5                   10                  15

Asn Asn Tyr His Arg Tyr Ser Gly Met Gly Phe Gly Pro Glu Thr Pro
            20                  25                  30

(2) INFORMATION FOR SEQ ID NO: 47:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 47:

AGCTTTCGTT GACGACGACG ATATCTTA                          28

(2) INFORMATION FOR SEQ ID NO: 48:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO: 48:

AAGCAACTGC TGCTGCTATA GAATCGA                           27

(2) INFORMATION FOR SEQ ID NO: 49:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 49:

Phe Val Asp Asp Asp Asp Asn
1               5

(2) INFORMATION FOR SEQ ID NO: 50:

(i) SEQUENCE CHARACTERISTICS:
        (A) LENGTH: 7 amino acids
        (B) TYPE: amino acid
        (C) STRANDEDNESS: <Unknown>
        (D) TOPOLOGY: linear (ii) MOLECULE TYPE: peptide (xi) SEQUENCE DESCRIPTION: SEQ ID NO: 50:

Met Val Asp Asp Asp Asp Asn
1               5

(2) INFORMATION FOR SEQ ID NO: 51:

(i) SEQUENCE CHARACTERISTICS:
        (A) LENGTH: 24 amino acids
        (B) TYPE: amino acid
        (C) STRANDEDNESS: <Unknown>
        (D) TOPOLOGY: linear (ii) MOLECULE TYPE: peptide (ix) FEATURE:
        (A) NAME/KEY: Modified-site
        (B) LOCATION: 2
        (D) OTHER INFORMATION: /note= "Xaa is Lys, Thr or Ala"

(ix) FEATURE:
        (A) NAME/KEY: Modified-site
        (B) LOCATION: 3
        (D) OTHER INFORMATION: /note= "Xaa is Leu or Tyr"

(ix) FEATURE:
        (A) NAME/KEY: Modified-site
        (B) LOCATION: 4
        (D) OTHER INFORMATION: /note= "Xaa is Ser, Thr or Trp"

```
(ix) FEATURE:
    (A) NAME/KEY: Modified-site
    (B) LOCATION: 5
    (D) OTHER INFORMATION: /note= "Xaa is Gln, Lys or Arg"

(ix) FEATURE:
    (A) NAME/KEY: Modified-site
    (B) LOCATION: 6
    (D) OTHER INFORMATION: /note= "Xaa is Glu, Asp or Asn"

(ix) FEATURE:
    (A) NAME/KEY: Modified-site
    (B) LOCATION: 7
    (D) OTHER INFORMATION: /note= "Xaa is Leu or Phe"

(ix) FEATURE:
    (A) NAME/KEY: Modified-site
    (B) LOCATION: 8
    (D) OTHER INFORMATION: /note= "Xaa is His or Asn"

(ix) FEATURE:
    (A) NAME/KEY: Modified-site
    (B) LOCATION: 9
    (D) OTHER INFORMATION: /note= "Xaa is Lys or Asn"

(ix) FEATURE:
    (A) NAME/KEY: Modified-site
    (B) LOCATION: 10
    (D) OTHER INFORMATION: /note= "Xaa is Leu, Tyr or Phe"

(ix) FEATURE:
    (A) NAME/KEY: Modified-site
    (B) LOCATION: 11
    (D) OTHER INFORMATION: /note= "Xaa is Gln or His"

(ix) FEATURE:
    (A) NAME/KEY: Modified-site
    (B) LOCATION: 12
    (D) OTHER INFORMATION: /note= "Xaa is Thr or Arg"

(ix) FEATURE:
    (A) NAME/KEY: Modified-site
    (B) LOCATION: 13
    (D) OTHER INFORMATION: /note= "Xaa is Tyr or Phe"

(ix) FEATURE:
    (A) NAME/KEY: Modified-site
    (B) LOCATION: 14
    (D) OTHER INFORMATION: /note= "Xaa is Pro or Ser"

(ix) FEATURE:
    (A) NAME/KEY: Modified-site
    (B) LOCATION: 15
    (D) OTHER INFORMATION: /note= "Xaa is Arg, Gly or Gln"

(ix) FEATURE:
    (A) NAME/KEY: Modified-site
    (B) LOCATION: 16
    (D) OTHER INFORMATION: /note= "Xaa is Thr or Met"

(ix) FEATURE:
    (A) NAME/KEY: Modified-site
    (B) LOCATION: 17
    (D) OTHER INFORMATION: /note= "Xaa is Asp, Ala, Gly or
        Asn"

(ix) FEATURE:
    (A) NAME/KEY: Modified-site
    (B) LOCATION: 18
    (D) OTHER INFORMATION: /note= "Xaa is Val, Leu, Ile, Phe
        or Thr"

(ix) FEATURE:
    (A) NAME/KEY: Modified-site
    (B) LOCATION: 20
    (D) OTHER INFORMATION: /note= "Xaa is Ala, Val, Pro or
        Ser"
```

-continued

```
    (ix) FEATURE:
        (A) NAME/KEY: Modified-site
        (B) LOCATION: 21
        (D) OTHER INFORMATION: /note= "Xaa is Gly, Val or Glu"

(ix) FEATURE:
        (A) NAME/KEY: Modified-site
        (B) LOCATION: 22
        (D) OTHER INFORMATION: /note= "Xaa is Thr, Val or Ala"

(ix) FEATURE:
        (A) NAME/KEY: Modified-site
        (B) LOCATION: 24
        (D) OTHER INFORMATION: /note= "Xaa is any amino acid"

(xi) SEQUENCE DESCRIPTION: SEQ ID NO: 51:

Gly Xaa Xaa Xaa Xaa Xaa Xaa Xaa Xaa Xaa Xaa Xaa Xaa Xaa Xaa Xaa
1               5                   10                  15

Xaa Xaa Gly Xaa Xaa Xaa Pro Xaa
                20
```

RECOMBINANT PREPARATION OF CALCITONIN FRAGMENTS AND USE THEREOF IN THE PREPARATION OF CALCITONIN AND RELATED ANALOGS

This application is a Divisional of application Ser. No. 09/139,819 filed Aug. 25, 1998, now U.S. Pat. No. 6,251,635 which is a Divisional of application Ser. No. 08/595,868 filed Feb. 6, 1996, now U.S. Pat. No. 5,962,270.

Calcitonins and related analogs, such as Elcatonin, are known polypeptides which can be employed for treating bone atrophy (see, e.g., U.S. Pat. No. 4,086,221). Naturally occurring calcitonins, such as eel, salmon or human calcitonin, are C-terminal amidated polypeptides which consist of 32 amino acids, the first and the seventh amino acids in each case being L-cysteines whose mercapto groups are connected to each other by the formation of a disulfide bridge. The natural calcitonins can be obtained, for example, by extraction from the mammalian thyroid gland (see, e.g., U.S. Pat. No. 5,428,129).

Elcatonin is a modified synthetic "carba" analog of calcitonin whose activity is comparable with that of eel calcitonin (Morikawa et al., *Experienta,* 32, 1004, (1976)). In contrast to eel calcitonin, Elcatonin lacks an amino terminal end and the disulfide bridge of eel calcitonin has been replaced by a —(CH$_2$)$_5$— "carbon bridge."

Currently, a variety of processes are known for the preparation of Elcatonin using purely chemical methods. These chemical methods involve condensation of the corresponding amino acids or peptides (see, e.g., U.S. Pat. Nos. 4,086,221 and 5,428,129). The purely chemical methods, however, all suffer from the disadvantage that, due to the elaborate purification methods required, the Elcatonin is obtained in low yield and its preparation is consequently very expensive.

It would accordingly be beneficial to be able to avoid the disadvantages of the purely chemical methods in the preparation of Elcatonin through the use of a approach which includes the recombinant preparation of a portion of the molecule. This could be achieved, for example, if a simple process for the recombinant preparation of a C-terminal polypeptide fragment was available. The recombinantly synthesized C-terminal fragment could then be used as a starting peptide for the preparation of calcitonin or carba analogs such as Elcatonin. A partially recombinant strategy would also facilitate the synthesis of peptides/peptide analogs of calcitonin, Elcatonin and related analogs or derivatives which could potentially include non-natural amino acids.

SUMMARY OF THE INVENTION

The present invention is directed to a process for the recombinant preparation of a calcitonin fragment and the use of the fragment in the preparation of calcitonin and related analogs including carba analogs (referred to hereinafter as "calcitonin carba analogs"), such as Elcatonin. The invention includes recombinantly forming a fusion protein which includes a target sequence linked to a carbonic anhydrase through a cleavage site. The target sequence includes a sequence of at least about 15 amino acids residues corresponding to a fragment from near the C-terminus of calcitonin or to a closely related analog of such a fragment. Typically, the target sequence includes an amino acid sequence corresponding to amino acids residues 10 through 32 of calcitonin or closely related analogs (collectively referred to hereinafter as a "10-32 fragment"). The recombinantly formed fusion protein is subsequently cleaved with a cleavage reagent to produce a polypeptide including the target sequence. The cleavage reaction may be carried out by contacting the fusion protein with either a chemical cleavage reagent or an enzymatic cleavage reagent. The choice of a suitable cleavage reagent and the corresponding cleavage site incorporated into the fusion protein will depend on the particular target sequence and carbonic anhydrase sequence present in the fusion protein. Typically, the cleavage reagent and cleavage site are selected such that the amino acid sequence constituting the cleavage site does not appear in the amino acid sequence of either the target sequence or the carbonic anhydrase. For example, a cyanogen bromide cleavage at methionine would not be employed with a fusion protein which included the 10-32 fragment from porcine, bovine or sheep calcitonin.

The cleavage site is typically present in a linker sequence which connects the carbonic anhydrase and the target sequence. Alternatively, the fusion protein may include a construct in which the C-terminus of the carbonic anhydrase is connected directly to the N-terminus of the target sequence. This may occur where the C-terminal residue(s) of the carbonic anhydrase and the N-terminal residue(s) of the target sequence constitute a cleavage site which allows cleavage of the peptide bond between the two fragments. In addition to a cleavage site present in a linker sequence, the carbonic anhydrase portion of the fusion protein may also include a different cleavage site which permits the fusion protein to be cleaved to form a "minifusion protein," i.e., a polypeptide having a C-terminal portion of the carbonic anhydrase still linked to the target sequence.

One embodiment of the invention includes a method for the recombinant preparation of polypeptides corresponding to amino acids 10-32 of calcitonin or related analogs ("10-32 fragments"). The method typically includes the recombinant preparation of a polypeptide fragment ("10-32 fragment-Xxxx") of the formula:

$A_{10}$-$A_{11}$-$A_{12}$-$A_{13}$-$A_{14}$-$A_{15}$-$A_{16}$-$A_{17}$-$A_{18}$-$A_{19}$-$A_{20}$-$A_{21}$-$A_{22}$-$A_{23}$-$A_{24}$-$A_{25}$-$A_{26}$-$A_{27}$-Gly-$A_{29}$-$A_{30}$-$A_{31}$-Pro-Xxx (SEQ ID NO:1)

wherein $A_{10}$ is Gly or Ser, $A_{11}$ is Lys, Thr or Ala, $A_{12}$ is Leu or Tyr, $A_{13}$ is Ser, Thr or Trp, $A_{14}$ is Gln, Lys or Arg, $A_{15}$ is Glu, Asp or Asn, $A_{16}$ is Leu or Phe, $A_{17}$ is His or Asn, $A_{18}$ is Lys or Asn, $A_{19}$ is Leu, Tyr or Phe, $A_{20}$ is Gln or His, $A_{21}$ is Thr or Arg, $A_{22}$ is Tyr or Phe, $A_{23}$ is Pro or Ser, $A_{24}$ is Arg, Gly or Gln, $A_{25}$ is Thr or Met, $A_{26}$ is Asp, Ala, Gly, or Asn, $A_{27}$ is Val, Leu, Ile, Phe, or Thr, $A_{29}$ is Ala, Val, Pro or Ser, $A_{30}$ is Gly, Val or Glu, $A_{31}$ is Thr, Val or Ala. The C-terminal -Xxx group is typically a C-terminal carboxylic acid ("—OH"), a C-terminal carboxamide ("—NH$_2$"), or group capable of being converted into a C-terminal carboxamide, such as an amino acid residue or a polypeptide group (typically having from 2 to about 10 amino acid residues). The 10-32 fragment represented by residues $A_{10}$ to $A_{32}$ (SEQ ID NO:2) corresponds to residues 10 through 32 of the amino acid sequences for eel (SEQ ID NO:37), salmon I (SEQ ID NO:38), salmon II (SEQ ID NO:39), salmon III (SEQ ID NO:40), chicken (SEQ ID NO:41), human (SEQ ID No:42), rabbit (SEQ ID NO:43), porcine (SEQ ID NO:44), bovine (SEQ ID NO:45) and sheep (SEQ ID NO:46) calcitonin or closely related analogs (see the calcitonin sequences shown in FIG. 9). The present method may also be employed to recombinantly produce 10-32 fragments corresponding to modified calcitonin sequences. The modified calcitonin sequences may include one or more conservative amino acid substitutions in the natural amino acid sequence.

The 10-32 fragment may be utilized in the preparation of calcitonin and related analogs. The preparation typically includes the condensation of an N-terminal fragment of the formula:

(SEQ ID NO: 3)

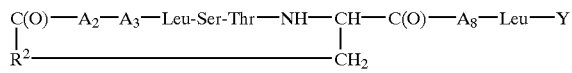

wherein $A_2$ is Gly, Ser or Ala; $A_3$ is Asn or Ser; $A_8$ is Val or Met; $R^2$ is —$(CH_2)_4$— or —$CH(NH_2)CH_2S$—S—; and Y is OH, $OR^1$, where —$R^1$ is a lower alkyl group;

with a recombinantly-formed polypeptide of the formula:

$A_{10}$-$A_{11}$-$A_{12}$-$A_{13}$-$A_{14}$-$A_{15}$-$A_{16}$-$A_{17}$-$A_{18}$-$A_{19}$-$A_{20}$-$A_{21}$-$A_{22}$-$A_{23}$-$A_{24}$-$A_{25}$-$A_{26}$-$A_{27}$-Gly-$A_{29}$-$A_{30}$-$A_{31}$-Pro-Xxx (SEQ ID NO:1)

wherein a $A_{10}$ is Gly or Ser, $A_{11}$ is wherein $A_{10}$ is Gly or Ser, $A_{11}$ is Lys, Thr or Ala, $A_{12}$ is Leu or Tyr, $A_{13}$ is Ser, Thr or Trp, $A_{14}$ is Gln, Lys or Arg, $A_{15}$ is Glu, Asp or Asn, $Al_{16}$ is Leu or Phe, $A_{17}$ is His or Asn, $A_{18}$ is Lys or Asn, $A_{19}$ is Leu, Tyr or Phe, $A_{20}$ is Gln or His, $A_{21}$ is Thr or Arg, $A_{22}$ is Tyr or Phe, $A_{23}$ is Pro or Ser, $A_{24}$ is Arg, Gly or Gln, $A_{25}$ is Thr or Met, $A_{26}$ is Asp, Ala, Gly, or Asn, $A_{27}$ is Val, Leu, Ile, Phe, or Thr, $A_{29}$ is Ala, Val, Pro or Ser, $A_{30}$ is Gly, Val or Glu, $A_{31}$ is Thr, Val or Ala, and -Xxx is —OH, —$NH_2$, an amino acid residue or a polypeptide group;

in the presence of a non-enzymatic coupling reagent to form a calcitonin-derivative having the formula:

(SEQ ID NO: 4)

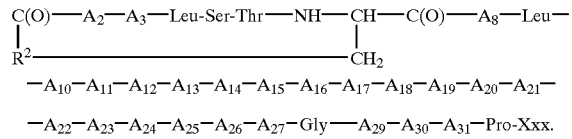

In one embodiment of the invention, the recombinantly-formed 10-32 fragment is condensed with a desaminononapeptide. The desaminononapeptide is a carba analog of an N-terminal calcitonin fragment and typically has the formula:

(SEQ ID NO: 3)

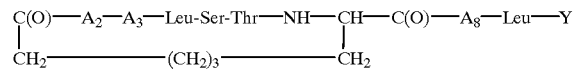

wherein $A_2$ is Gly, Ser or Ala; $A_3$ is Asn or Ser; $A_8$ is Val or Met; and Y is OH, $OR^1$, where —$R^1$ is a lower alkyl group (i.e., a $C_1$-$C_6$ alkyl group). The condensation reaction may be carried out using a chemical coupling reaction such as those described in U.S. Pat. Nos. 4,086,221 and 5,428,129, the disclosures of which are herein incorporated by reference. Chemical coupling agents are well known to those skilled in the art. Suitable chemical coupling agents include carbodiimides and a variety of other non-enzymatic reagents capable of reacting with the α-carboxylic acid group of a peptide to form an activated carboxylic acid derivative and/or capable of catalyzing the condensation of an activated α-carboxylic acid derivative with an N-terminal α-amino group of another amino acid or polypeptide. Chemical coupling reactions in which the C-terminal α-carboxylic acid of the desaminononapeptide has been converged to an acid azide, mixed acid anhydride, acid imidazole or active ester may be employed in the present invention. An especially effective method of coupling two peptide fragments is carried out in the presence of a carbodiimide and a reagent capable of forming an active ester, e.g., a mixture of dicyclohexylcarbodiimide ("DCC") and either N-hydroxysuccinimide ("HOSu") or 1-hydroxybenzotriazole ("HOBt").

The recombinantly-formed 10-32 fragment employed in the condensation preferably has the formula:

$A_{10}$-$A_{11}$-$A_{12}$-$A_{13}$-$A_{14}$-$A_{15}$-$A_{16}$-$A_{17}$-$A_{18}$-$A_{19}$-$A_{20}$-$A_{21}$-$A_{22}$-$A_{23}$-$A_{24}$-$A_{25}$-$A_{26}$-$A_{27}$-Gly-$A_{29}$-$A_{30}$-$A_{31}$-Pro-Xxx (SEQ ID NO:1)

wherein $A_{10}$ through $A_{31}$ and -Xxx are as defined herein.

The product of the coupling reaction is typically a calcitonin carba analog having the formula:

(SEQ ID NO: 4)

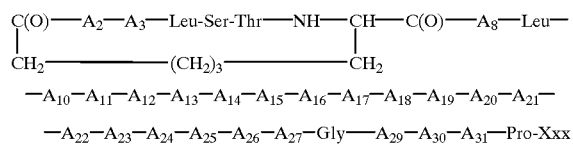

wherein $A_{10}$ through $A_{31}$ and -Xxx are the same as defined herein for the desaminononapeptide (SEQ ID NO:3) or the 10-32 fragment-Xxx (SEQ ID NO:1). The coupling of the desaminononapeptide and the recombinantly-formed peptide is typically carried out in the presence of a non-enzymatic coupling reagent.

A preferred embodiment of the invention provides a method for the recombinant preparation and amidation of a polypeptide fragment (referred to herein as the "ECF2-amide") having the formula:

Gly-Lys-Leu-Ser-Gln-Glu-Leu-His-Lys-Leu-Gln-Thr-Tyr-Pro-Arg-Thr-Asp-Val-Gly-Ala-Gly-Thr-Pro-$NH_2$ (SEQ ID NO:6)

and for coupling the ECF2-amide to an amino terminal fragment of Elcatonin (referred to hereafter as "ECF1"), which has the formula:

(SEQ ID NO: 7)

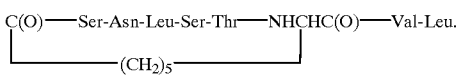

The present invention also provides a nucleic acid sequence which includes a sequence coding for amino acids 10-32 of calcitonin or a related analog. The nucleic acid sequence typically encodes a fusion protein which includes the 10-32 fragment linked to a carbonic anhydrase through a cleavage site. The portion of the gene encoding the 10-32 fragment is preferably designed using optimal codon usage for a targeted host cell, such as *E. coli, S. cerevisiae* or *P. pastoris*.

BRIEF DESCRIPTION OF THE DRAWINGS

FIG. 6A shows the nucleotide (SEQ ID NO:11) and amino acid (SEQ ID NO:12) sequences for the N-terminal methionine and hCAII residues 1-162 of the hCAII-Linker-ECF2-Ala fusion protein construct.

FIG. 6B shows the nucleotide (SEQ ID NO:11) and amino acid (SEQ ID NO:12) sequences for hCAII residues 162-257, and the linker and ECF2-Ala fragments of the hCAII-Linker-ECF2-Ala fusion protein construct.

FIG. 9A shows the amino acid sequences for residues 1-15 of calcitonin from a number of species.

FIG. 9B shows the amino acid sequences for residues 16-32 of calcitonin from a number of species.

FIG. 10 shows a double stranded DNA fragment (SEQ ID NO:10) synthesized from the 5 oligonucleotide described in example 1.1 via PCR methodology.

FIG. 11 depicts the nucleotide sequence for oligonucleotide $2^{Ext}$ (SEQ ID NO:8) produced during the PCR synthesis of the gene sequence encoding ECF2.

FIG. 12 depicts the nucleotide sequence for oligonucleotide $3^{Ext}$ (SEQ ID NO:9) produced during the PCR synthesis of the gene sequence encoding ECF2.

DETAILED DESCRIPTION OF THE INVENTION

Figure 1:
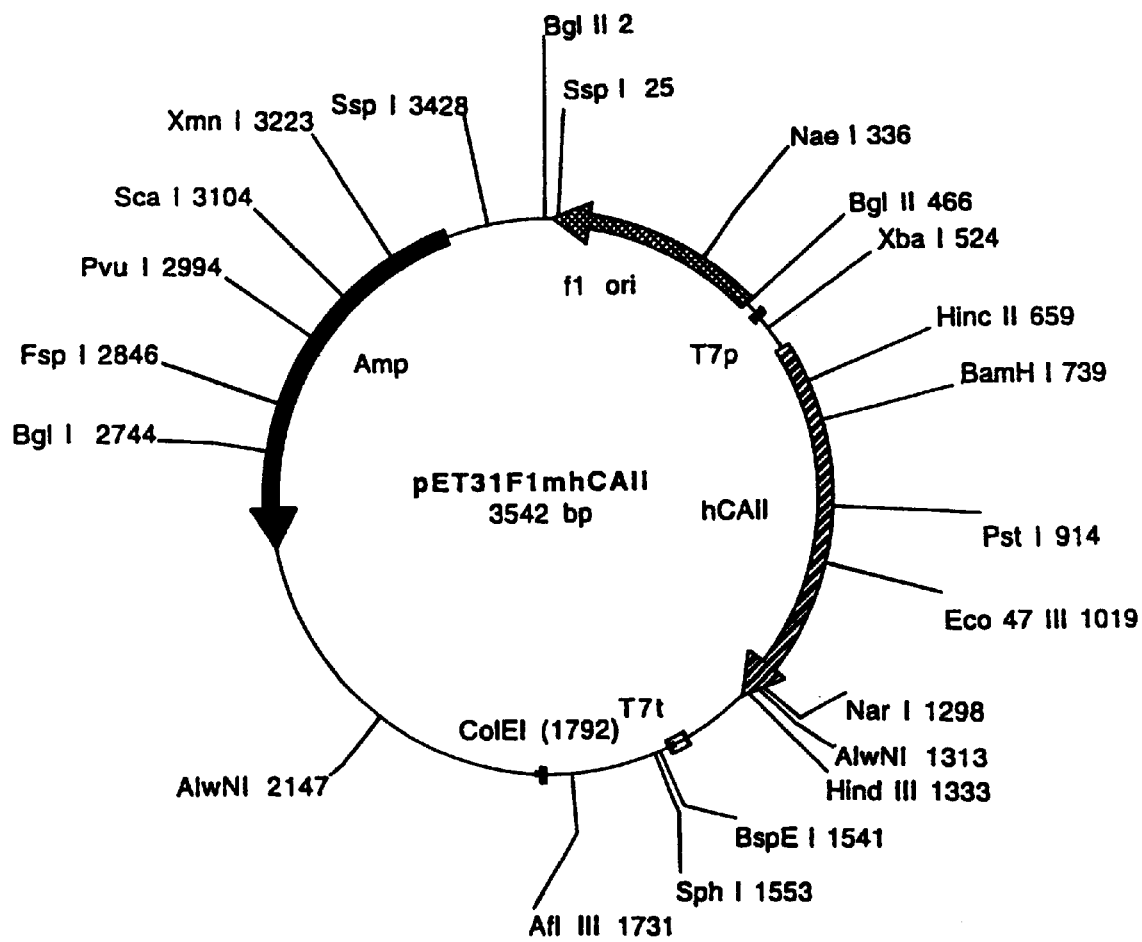
FIG. 1 shows a map of plasmid pET31F1mhCAII. The plasmid includes the F1 origin of replication from plasmid pEMBL8 introduced in the opposite orientation of the pSP65 origin of replication.

The recombinant preparation of the fusion protein according to the present invention includes the construction of a nucleic acid sequence coding for the target sequence linked to a carbonic anhydrase through a cleavage site ("FP nucleic acid sequence"). The FP nucleic acid sequence shown in FIG. 6 is one example of a suitable nucleic acid sequence for use in the present method. The nucleic acid sequence shown in FIG. 6 includes codons encoding residues 1-257 of human carbonic anhydrase II ("hCAII").

Inclusion of this amino acid sequence or other functionally active fragments of a carbonic anhydrase in the fusion protein greatly facilitates the isolation of the fusion protein from cell debris. As used herein, the term "carbonic anhydrase" includes naturally occurring carbonic anhydrase (and any allelic variants), functionally active carbonic anhydrase fragments or modified versions ("mutants") thereof. Herein "functionally active carbonic anhydrase fragments and mutants" means a fragment or modified version of a carbonic anhydrase which exhibits the enzyme inhibitor binding properties of hCAII. Fragments having such properties are capable of binding carbonic anhydrase inhibitors such as sulfanilamides extremely tightly. A functionally active fragment having such binding properties exhibits highly selective affinity binding to a low molecular weight ligand, e.g. a sulfanilamide, or a synthetic derivative thereof. The binding is strong so that, in general, the carbonic anhydrase/ligand conjugate will exhibit a solution dissociation constant (inverse of the binding constant) of no more than about $10^{-7}$M. Generally, the ligand is a reversible inhibitor for the carbonic anhydrase. Suitable carbonic anhydrase fragments may lack an N-terminal or C-terminal portion of the enzyme, so long as the fragments retain the functional inhibitor binding activity of the enzyme. Similarly, modified carbonic anhydrases which may be employed as binding proteins in the present fusion protein may be modified by one or more amino acid additions, deletions or insertions so long as the modified enzyme substantially exhibits the inhibitor binding activity described above. Typically, a carbonic anhydrase is modified by deleting or altering amino acid residues so that the modified enzyme does not contain the particular amino acid(s) to be employed as a cleavage site in the fusion protein. For example, where cyanogen bromide is to be utilized as a cleavage reagent, a carbonic anhydrase may be modified to remove or replace any methionine ("Met") residues normally present.

The FP nucleic acid sequence includes a sequence encoding a 10-32 fragment, i.e., amino acid residues 10-32 of calcitonin or a closely related analog. The closely related analogs may be derived from conservative amino acid substitutions in a calcitonin 10-32 fragment. This portion of the nucleic acid sequence may be designed to optimize the expression of the fusion protein in a particular host cell. For example, where the expression of the fusion protein is to be carried out using an enterobacteria such as *E. coli* as the host organism, the nucleic acid sequences encoding the 10-32 fragment and the cleavage site are typically constructed based on the frequency of codon usage for the targeted host organism (see, e.g., discussion of frequency of codon usage in Gribskov et al., *Nucl. Acids Res.*, 12, 539-549 (1984)).

The cleavage site may be a chemical cleavage site or an enzymatic cleavage site. Chemical and enzymatic cleavage sites and the corresponding agents used to effect cleavage of a peptide bond close to one of these sites are described in detail in PCT patent application WO 92/01707, the disclosure of which is herein incorporated by reference. Examples of peptide sequences (and DNA gene sequences coding therefor) suitable for use as cleavage sites in the present invention and the corresponding cleavage enzymes or chemical cleavage conditions are shown in Table 1. The gene sequence indicated is one possibility coding for the corresponding peptide sequence. Other DNA sequences may be constructed to code for the same peptide sequence. Preferably, the nucleic acid sequence coding for the cleavage site is designed based on the more commonly used codons for each amino acid for the host cell to be employed in the expression of the fusion protein. For example, The nucleotide sequence may be based on optimum codon usage for an enterobacteria, such as *E. coli* (see, e.g., Gribskov et al., *Nucl. Acids Res.*, 12, 539-549 (1984)).

The cleavage site may be present as part of a linker peptide which connects the carbonic anhydrase and the target sequence. For example, the amino acid sequence (SEQ ID NO:12) for hCAII-linker-ECF2-Ala ("hCA-ECF2-Ala") depicted in FIG. 6 includes a seven amino acid linker sequence (-Phe-Val-Asp-Asp-Asp-Asp-Asn-; (SEQ ID NO:14)) which sets up a chemical cleavage site cleavable by hydroxylamine ("Asn-Gly") between the C-terminal asparagine residue of the linker and the N-terminal glycine residue of the target sequence.

The fusion protein includes at least one copy and may include multiple copies of the target sequence. Where multiple copies of the target sequence are present, the copies may be tandemly linked together. Alternatively, the copies of the target sequence may be linked together by an innerconnecting linker peptide. The innerconnecting linker peptide may be the same as or different than the intraconnecting linker peptide which connects the carbonic anhydrase to the first copy of the target peptide. If the innerconnecting and intraconnecting linker peptides are the same or include the same cleavage site, the fusion protein may be cleaved directly to produce a number of fragments each containing a single copy of the target peptide. If, however, the innerconnecting and intraconnecting linker peptides contain different cleavage sites, it may be possible to initially cleave off the carbonic anhydrase fragment to form a intermediate polypeptide having more than one copy of the target peptide.

TABLE 1

| | Peptide Sequence | DNA Sequence |
|---|---|---|
| Enzymes for Cleavage | | |
| Enterokinase | (Asp)₄Lys (SEQ ID NO: 16) | GACGACGACGATAAA (SEQ ID NO: 15) |
| Factor Xa | IleGluGlyArg (SEQ ID NO: 18) | ATTGAAGGAAGA (SEQ ID NO: 17) |
| Thrombin | GlyProArg or GlyAlaArg | GGACCAAGA or GGAGCGAGA |
| Ubiquitin Cleaving Enzyme | ArgGlyGly | AGAGGAGGA |
| Renin | HisProPheHisLeu-LeuValTyr (SEQ ID NO: 20) | CATCCTTTTCATC-TGCTGGTTTAT (SEQ ID NO: 19) |
| Trypsin | Lys or Arg | AAA OR CGT |
| Chymotrypsin | Phe or Tyr or Trp | TTT or TAT or TGG |
| Clostripain | Arg | CGT |
| *S. aureus* V8 | Glu | GAA |
| Chemical Cleavage | | |
| (at pH3) | AspGly or AspPro | GATGGA or GATCCA |
| (Hydroxylamine) | AsnGly | AATCCA |
| (CNBr) | Methionine | ATG |
| BNPS-skatole | Trp | TGG |
| 2-Nitro-5-thiocyanatobenzoate | Cys | TGT |

Target sequences free of methionine residues may be produced using the present method from a multicopy construct having innerconnecting peptides which include a methionine residue. Where the methionine residue is directly linked to the C-terminus of the target sequence, the multicopy construct may be cleaved with cyanogen bromide. The resulting fragments may be transpeptidated using a carboxypeptidase, e.g., a serine carboxypeptidase such as carboxypeptidase Y, to replace the C-terminal homoserine residue with an α-amidated amino acid. The fragments may be also transamidated with the carboxypeptidase to replace the C-terminal homoserine residue with a 2-nitrobenzylamine compound. This produces a fragment having a C-terminal (2-nitrobenzyl)amido group which may be photochemically decomposed to produce an α-amidated peptide fragment minus the homoserine residue.

One example of a fusion protein including multiple copies of a target sequence in a construct which includes hCA-(MetValAspAspAspAspAsn-ECF2)$_n$-Xxx (SEQ ID NO: 50), where hCA, ECF2 and Xxx are as defined herein and n is an integer (typically 2 to 20). Such a construct may be treated with CNBr to form ValAspAspAspAspAsn-ECF2-Hse (SEQ ID NO:49) peptide fragments (where Hse is a homoserine residue produced by the reaction of CNBr with a Met residue). The peptide fragments may then be reacted with a nucleophile such as o-nitrophenylglycine amide ("ONPGA") in the presence of a peptidase such as carboxypeptidase Y resulting in the replacement of the Hse residue by ONPGA. Upon photolysis, the transpeptidation product is converted to a C-terminal carboxamide. The N-terminal tail sequence, ValAspAspAspAspAsn (SEQ ID NO:49), may be cleaved off the fragments by treatment with hydroxylamine.

A preferred embodiment of the invention is directed to the preparation of the C-terminal eel calcitonin polypeptide fragment, ECF2-amide (SEQ ID NO:6). The preparation involves the initial genetic expression of the following protein construct:

Met-hCAII'-Met$_{240}$-Val$_{241}$-hCAII"-Linker-ECF2-aa ("hCA-ECF2-aa")

where aa is an amino acid residue and Met is the required N-terminal residue of any *E. coli* protein. The Met residue is added to the N-terminus of the first residue of hCAII' (a 239 amino acid N-terminal polypeptide segment of human carbonic anhydrase II), Met$_{240}$-Val$_{241}$ is the only cyanogen bromide labile peptide bond in human carbonic anhydrase II ("hCAII"), hCAII" is a 16 amino acid fragment (SEQ ID NO:21) from near the C-terminal end of hCAII (residues 242-257). The C-terminal amino acid residue of ECF2-aa (SEQ ID NO:22), designated aa, provides an amidation signal to enable conversion to the Pro-amide that constitutes the C-terminus of Elcatonin (SEQ ID NO:13). The aa residue is typically an amino acid residue, such as alanine, which is capable of being exchanged with a nucleophile via a transamidation reaction.

The desired product, ECF2-aa (SEQ ID NO:22), can be obtained from a hCA-ECF2-aa protein construct, in at least two ways. The first employs a cleavage of hCA-ECF2-aa at the Asn-Gly bond with hydroxylamine to yield ECF2-aa (SEQ ID NO:22) directly. Alternatively, cleavage with cyanogen bromide (CNBr) yields a minifusion protein which includes the hCAII" C-terminal fragment (SEQ ID NO:21) of hCAII linked to the ECF2-aa polypeptide (SEQ ID NO:22). The minifusion protein may subsequently be cleaved with hydroxylamine either before derivatization to provide ECF2-aa (SEQ ID NC:22) or, after derivatization of the minifusion protein side chain residues, e.g., where the Lys residues of ECF2-aa (SEQ ID NO:22) have been derivatized to form Lys residues having Z-protected side chain amino groups. In the case where derivatization reagents modify the side chain amino functions of Lys, then after cleavage of derivatized minifusion protein, the resulting protected ECF2-aa (SEQ ID NO:22) produced will only possess a single free amino function at the alpha position of the N-terminal glycine residue. The free N-terminal a-amino group can be used for subsequent specific chemical reactions, such as coupling to the C-terminal residue of ECF1 (SEQ ID NO:7) to provide Elcatonin (SEQ ID NO:13). Coupling reactions of this type may be carried out after the ECF2-aa polypeptide (SEQ ID NO:22) has been converted to an ECF2 derivative having a C-terminal residue Pro-amide ("ECF2-amide"; (SEQ ID NO:6)), or may be employed to produce derivatized forms of Elcatonin (e.g., "Elcatonin-aa"; (SEQ ID NO:30)) for subsequent conversion to Elcatonin (SEQ ID NO:13).

A preferred sequence of ECF2-aa is:

Gly-Lys-Leu-Ser-Gln-Glu-Leu-His-Lys-Leu-Gln-Thr-Tyr-   ("ECF2-Ala"; SEQ ID NO:23)

Pro-Arg-Thr-Asp-Val-Gly-Ala-Gly-Thr-Pro-Ala

The ECF2-Ala peptide fragment may be derived from cleavage of a hCA-ECF2-Ala protein construct, e.g., by treatment with hydroxylamine. The hCA-ECF2-Ala protein construct may include the sequence:

hCAII'-Met-Val-Asp-Asn-Trp-Arg-Pro-Ala-Gln-Pro-Leu-Lys-   (SEQ ID NO:12)

Asn-Arg-Gln-Ile-Lys-Ala-Phe-Val-Asp-Asp-Asp-Asn-

Gly-Lys-Leu-Ser-Gln-Glu-Leu-His-Lys-Leu-Gln-Thr-Tyr-

Pro-Arg-Thr-Asp-Val-Gly-Ala-Gly-Thr-Pro-Ala

Alternatively, the hCA-ECF2-Ala protein construct may be cleaved at a different bond to produce a pre-ECF2-Ala peptide, i.e., a minifusion protein. For example, the hCA-ECF2-Ala protein construct may be cleaved to produce a pre-ECF2-Ala peptide which includes a C-terminal fragment of hCAII or a modified version thereof linked to the N-terminus of ECF2-Ala (SEQ ID NO:23). In a preferred embodiment of the invention, the hCA-ECF2-Ala protein construct (SEQ ID NO:12) may be cleaved with cyanogen bromide (CNBr) to yield a minifusion protein ("MFP") having the amino acid sequence:

Val-Asp-Asn-Trp-Arg-Pro-Ala-Gln-Pro-Leu-Lys-Asn-Arg-   (SEQ ID NO:24)

Glu-Ile-Lys-Ala-Phe-Val-Asp-Asp-Asp-Asn-Gly-Lys-

Leu-Ser-Gln-Glu-Leu-His-Lys-Leu-Gln-Thr-Tyr-Pro-Arg-

Thr-Asp-Val-Gly-Ala-Gly-Thr-Pro-Ala.

The MFP includes the $Val_{241}$-hCAII" fragment from the C-terminal end of hCAII:

Val-Asp-Asn-Trp-Arg-Pro-Ala-Gln-Pro-Leu-Lys-Asn-Arg-Glu-Ile-Lys-Ala   (SEQ ID NO:25)

and a Linker sequence having the formula:

Phe-Val-Asp-Asp-Asp-Asn   (SEQ ID NO:14).

The polypeptide segment hCAII'-$Met_{240}$-$Val_{241}$-hCAII" of human carbonic anhydrase II (hCAII) has been reported in Biochemistry, 9, 2638 (1970) and can be used as the binding protein segment for purification of a carbonic anhydrase-EGF2-aa protein construct using procedures such as those described in (WO 92/01707). In accordance with WO 92/01707, carbonic anhydrase fragments or modified carbonic anhydrases can also be used as the binding protein segment.

The amino acid sequences for a number of other carbonic anhydrases have also been reported (see, e.g., Hewett-Emmett et al., in *The Carbonic Anhydrases*, Dodgson et al. eds., Chapt. 2, pp. 15-32 (1991)). If the amino acid sequence of a particular carbonic anhydrase is known but no gene is available, a cDNA coding for the carbonic anhydrase may be isolated using procedures well known to those skilled in the art (see, e.g., Sambrook et al., *Molecular Cloning, A Laboratory Manual*, Cold Spring Harbor Laboratory, Cold Spring Harbor, N.Y. (1989), and Tanhauser et al., *Gene*, 117, 113-117 (1992)). This process typically includes constructing nucleic acids probes (e.g., about 20-30 base pairs in length) coding for fragments of the carbonic anhydrase in question. Degenerate nucleotide probes based on the known amino acid sequence or related DNA sequence can be used to screen a cDNA library (see, e.g., Wallace et al., *Nucleic Acids Res.*, 6, 3543 (1979) and Wallace et al., *Nucleic Acids Res.*, 9, 879 (1981)).

In another embodiment of the invention, the target sequence may include an amino acid sequence in which at least one of the C-terminal residues of a 10-32 fragment has been replaced by one or more amino acid residues ("leaving unit"). The C-terminal end of the target sequence may be modified via a transpeptidation reaction, either before or after cleavage of the fusion protein to remove the carbonic anhydrase portion. The transpeptidation reaction typically results in the removal of the leaving unit from the C-terminal end of the target sequence and its replacement by the missing C-terminal residue (or residues) of the "10-32 fragment." For example, a recombinantly produced peptide having C-terminal leaving unit, such as eel(10-30)-Ala (amino acid residues 10-30 of eel calcitonin coupled to a C-terminal alanine), may be transpeptidated using S. aureus V8 to introduce a Thr-Pro-NH$_2$ dieptide after residue Glu$_{30}$ in place of the C-terminal Ala residue.

In addition to being employed in the preparation of carba analogs of calcitonin, such as Elcatonin, the recombinantly synthesized 10-32 fragments of the present invention may be used in the synthesis of calcitonins. For example, a side chain protected derivative of ECF2-amide, e.g., where Ser, Thr and Glu residues are protected as benzyl ethers or esters and Lys residues are protected by a CBZ group, may be coupled using a non-enzymatic coupling reagent with the cyclic oxidized form of residues 1-9 of eel calcitonin. Examples of suitable non-enzymatic coupling reagents which may be used to carry out the coupling reaction include DCC, N-ethyl-N'-dimethylaminopropyl-carbodiimide ("EDAPC"), DCC/HOSu, DCC/HOBt and EDAPC/HOSu (see, e.g., U.S. Pat. No. 5,429,129, the disclosure of which is herein incorporated by reference).

I. Recombinant Formation of the Fusion Protein a. Vectors

Expression vectors incorporating the fusion protein gene are chosen to be compatible with the host cell. The vectors used have many features in common. These features include an origin so replication compatible with the host cell, regulatory DNA sequences for transcription and regulation of transcription (for inducible systems), an efficient ribosomal binding site (for prokaryotic hosts), a poly-A signal (for eukaryotic hosts). In addition, phenotype genes, regulatory regions and leader sequences may be included.

Prokaryotic vectors such as those for expression in E. coli are characterized by an origin of replication, a genetic marker (phenotype) for selection of transformed bacteria, and DNA regulation sequences that will direct the expression of the gene of interest. The regulation sequences typically will include a promoter to drive the transcription, an operator to control transcription (on/off switch), an efficient ribosome binding site to start translation, and a transcription termination signal. The start and stop codons are provided by the inserted (fusion protein) gene.

Prokaryotic vectors in particular contain a suitable "expression cassette" which is based upon any of a number of available promoter/operator systems. Typical promoters for inclusion in the prokaryotic vector include lactose, tryptophan, T7, lipoprotein, alkaline phosphatase, lambda leftward or rightward promoter or a combination of these (hybrid promoters). The lactose and tryptophan operators, as well as temperature sensitive lambda promoters are typical on/off switches that can be included in the prokaryotic vector. Typical phenotypic markers for inclusion in the prokaryotic vector include genes for development of resistance to ampicillin, tetracycline, kanamycin, and chloramphenicol.

Eukaryotic vectors such as those for expression in the yeast, Saccharomyces cerevisiae, typically are shuttle vectors which contain an origin of replication for E. coli and one for S. cerevisiae, a genetic marker for both cell types, and DNA regulation sequences that will direct the expression in yeast. The regulation sequences typically include a promoter, a regulatory sequence, and a transcription termination signal (including a polyadenylation signal). Optional signal sequences for direction of cellular secretion can also be inserted into the eukaryotic vector. Typical markers to be incorporated provide positive selection by complementation of mutations in the genes necessary for production of uracil, leucine, histidine, adenine, tryptophan and the like. Promoter sequences which preferably can be incorporated into the eukaryotic vector include alcohol dehydrogenase I or II, glyceraldehyde phosphate dehydrogenase, phosphoglycerokinase, galactose, tryptophan, mating factor alpha and the like.

Depending on the nature of the vector selected, the ECF2-aa gene fragment can be expressed in a variety of organisms. Both vectors having a specific host range and vectors having a broad host range are suitable for use in the present invention. Examples of vectors having a specific host range, e.g. for E. coli, are pBR322 (Bolivar et al., Gene, 2, 95-113, 1977), pUC18/19 (Yanisch Perron et al., Gene, 33, 103-119, 1985), pK18/19 (Pridmore, Gene, 56, 309-312, 1987), pRK290X (Alvarez-Morales et al., Nucleic Acids Res., 14, 4207-4227, 1986) and pRA95 (obtainable from Nycomed Pharm a AS, Huidove, Denmark).

Other vectors that can be employed are "broad host range" vectors which are suitable for use in Gram negative bacteria. Examples of such "broad host range" vectors are pRK290 (Ditta et al., Proc. Nat. Acad. Sci., 77, 7347-7351; 1980), pKT240 (Bagdasarian et al., Gene, 26, 273-282, 1983), derivatives of pRK290, such as pLAFR1 (Long et al., Nature, 289, 485-488, 1982), derivatives of pKT240, such as pMMB66EH (Furste et al., Gene, 48, 119-131, (1986)) or pGSS33 (Sharpe, Gene, 29, 93-102, (1984)).

b. Construction of Plasmid pTBN

An expression vector, pET31F1mhCAII, containing the hCAII gene was obtained from Dr. P. J. Laipis at the University of Florida. The ampicillin resistant, T7 expression vector was constructed by the method described in Tanhauser et al., Gene, 117, 113-117 (1992) from the plasmid pET-3c (Studier et al., Methods Enzymol., 185, 60-89 (1990)). The T7 expression cassette from the pET-3c vector was transferred to a truncated pSP65 plasmid. To enable the production of single stranded plasmid DNA, the F1 origin from pEMBL8+ (Dente et al., Nucleic Acids Res., 11, 1645-1655 (1983)) was ligated into the Bgl II restriction site of the positive clones. The resulting plasmid was designated pET31F1m, where F1m indicates that the F1 origin has the opposite orientation of the pSP65 origin of replication. Finally, human carbonic anhydrase II cDNA (hCAII cDNA) was cloned into the pET31F1m plasmid between the Nde± and BamH I sites to give a plasmid designated as pET31F1mhCAII (see FIG. 1).

The Linker region of the plasmid was created by first synthesizing two complementary oligonucleotides at the DNA Synthesis Core Facility of the Interdisciplinary Center for Biotechnology at the University of Florida:

5' A GCT TTC GTT GAC GAC GAC GAT ATC TT 3' (SEQ ID NO:26)

5' AGC TAA GAT ATC GTC GTC GTC AAC GAA 3' (SEQ ID NO:27)

Figure 2:
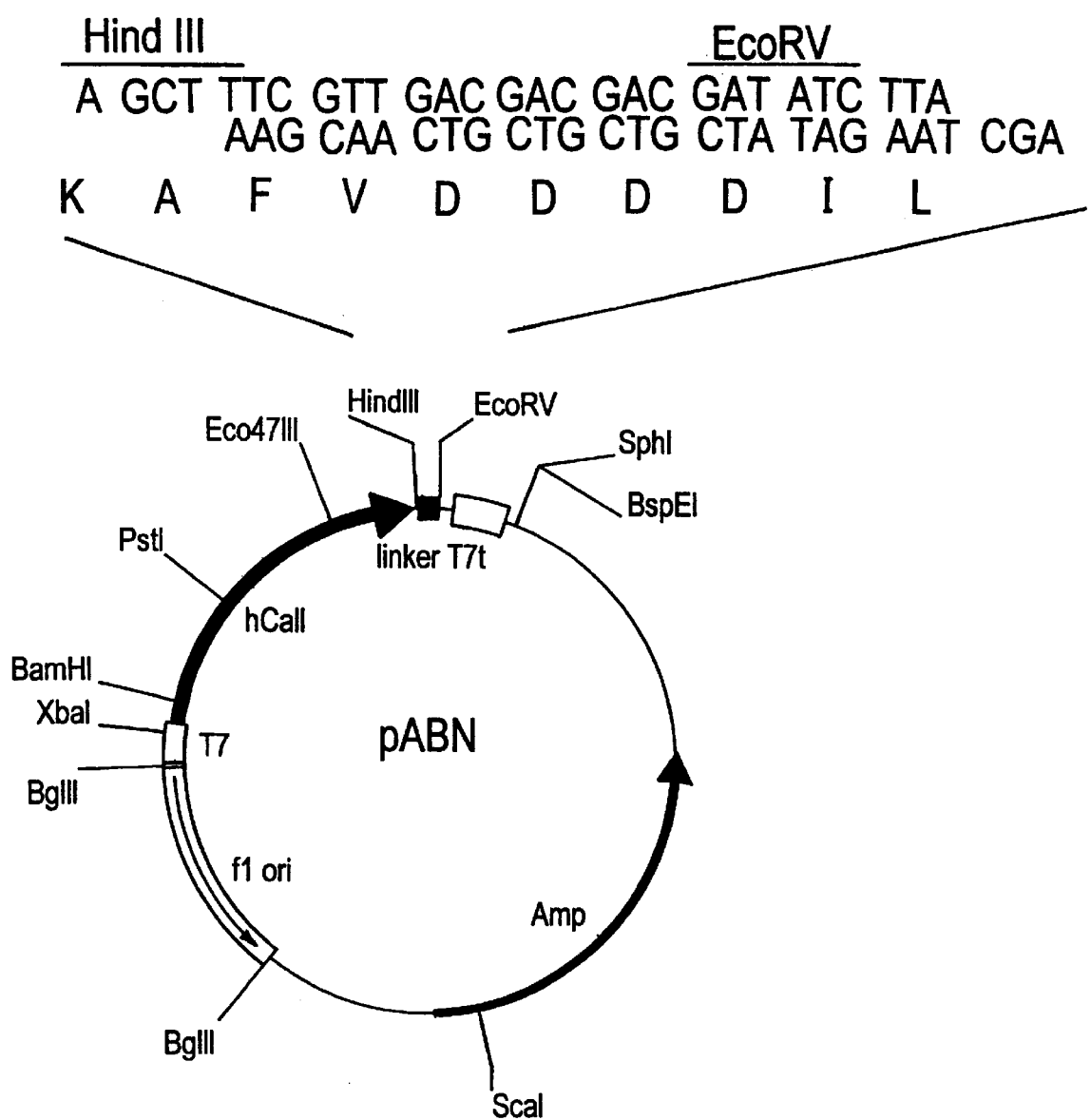
FIG. 2 shows a map of plasmid pABN. Plasmid pABN includes a nucleic acid sequence coding for a Linker peptide fragment inserted into the plasmid near the carboxy terminal end of the gene sequence of human carbonic anhydrase II ("hCAII").

The oligonucleotides were phosphorylated, annealed and ligated into the Hind III site near the carboxy terminal end of the gene sequence of hCAII. Plasmids containing the insert have a unique EcoR V site immediately following the fourth aspartic acid residue in the polypeptide fragment, Linker (SEQ ID NO:14). The resulting plasmid is referred to as pABN (see FIG. 2).

Figure 3:
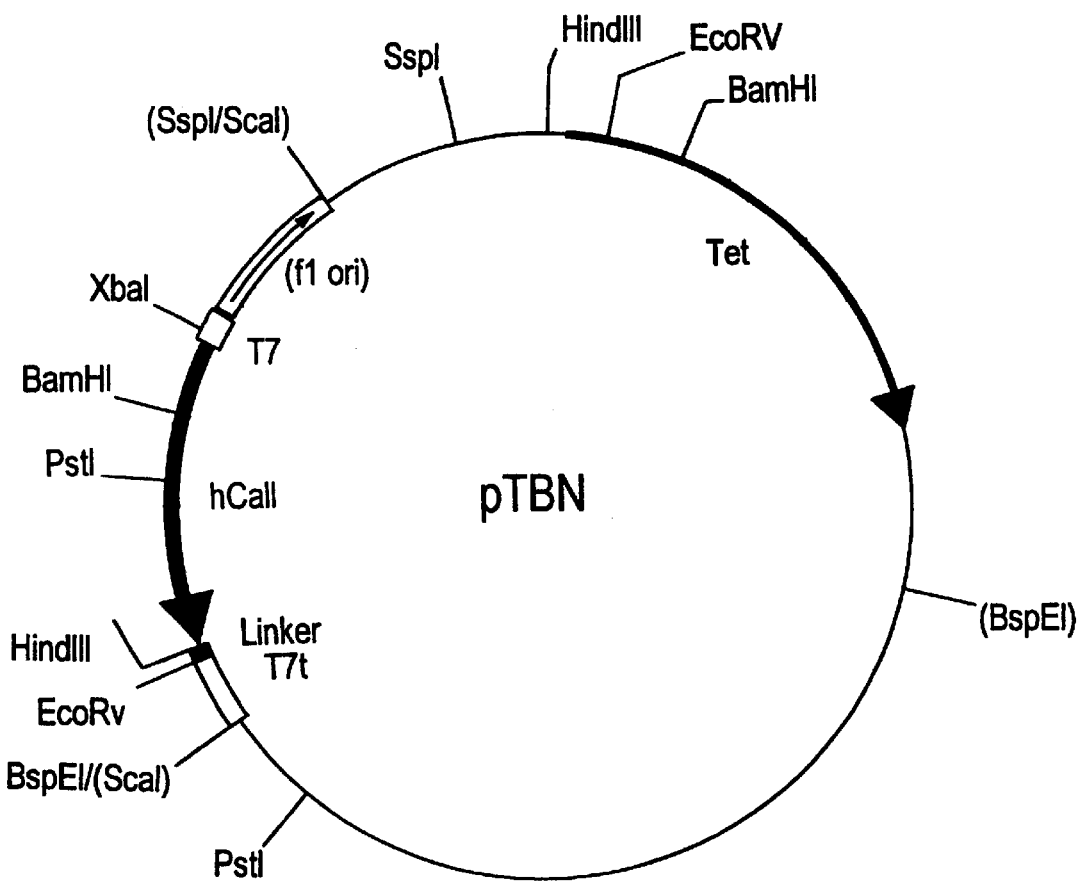
FIG. 3 shows a map of plasmid PTBN. Plasmid pTBN is a tetracycline resistant expression vector derived from the insertion of a 1.5-kb fragment from pABN into plasmid pBR322. The 1.5-kb fragment includes the T7 promotor, hCAII, Linker and T7 terminator sequences from pABN.

The plasmids pABN and pBR322 (Bolivar et al. Gene, 2, 95-113 (1977) were used to construct a tetracycline resistant expression vector to be used for the production of ECF2-aa (SEQ ID NO:27), e.g., where aa is Ala. The 1.5-kb Ssp I/BspE I fragment from pABN was inserted into the ScaI site of pBR322 resulting in pTBN (see FIG. 3).

c. Host Strains and Transformation

Procedures for methods to restrict, ligate, transform, select, culture, and lyse according to the invention, generally follow standard methods known in the art. Literature providing the details for these methods include, Sambrook et

```
hCAII'-Met-Val-Asp-Asn-Trp-Arg-Pro-Ala-Gln-Pro-Leu-Lys-   (SEQ ID NO:12)

Asn-Arg-Gln-Ile-Lys-Ala-Ser-Phe-Val-Asp-Asp-Asp-

Asn*-Gly-Lys-Leu-Ser-Gln-Glu-Leu-His-Lys-Leu-Gln-Thr-

Tyr-Pro-Arg-Thr-Asp-Val-Gly-Ala-Gly-Thr-Pro-Ala
``` al., *Molecular Cloning, A Laboratory Manual*, Cold Spring Harbor Laboratory, Cold Spring Harbor, N.Y. (1989), the disclosure of which is incorporated herein by reference.

In order to prepare the production strains for the fermentation, the DNA fragment encoding hCA-ECF2-aa is introduced into a host strain suitable for the expression of an hCA-ECF2 fusion protein. Examples of microorganisms which are suitable for expressing this gene typically include strains possessing a high tolerance of substrate and starting material, are enterobacteria, such as from the genus Escherichia. Microorganisms of the species *E. coli* are particularly preferred. The microorganisms can contain the hCA-ECF2-aa DNA fragment either on a vector molecule or integrated in their chromosomes. The selected microorganisms are transformed using methods well known to those skilled in the art (see, e.g. Sambrook et al., cited supra) with a vector containing the hCA-ECF2-aa DNA fragments. Examples of suitable production strains are *E. coli* JM109 (DE3) and *E. coli* BL21 (DE3), in each case containing a plasmid encoding the fusion protein, e.g., pTBN26.

The eukaryotic cells may include unicellular organisms, such as yeast cells, as well as immortal cells from higher organisms, such as plant, insect or mammalian cells. Suitable eukaryotic host cells include *Sacoharomyces cerevisiae, Pichia pastoris, Aspergillus niger, Spodoptera frupiperda*, and corn, tobacco or soybean plant cells. The higher organisms useful as hosts include higher order plants and animals having germ cells that are amenable to transformation. Included are plants such as tobacco, corn, soybean and fruit bearing plants, and invertebrate and vertebrate animals such as fish, birds and mammals, such as sheep, goats, cows, horses and pigs.

The transformed host strains are typically isolated from a selective nutrient medium to which an antibiotic has been added against which the host strains are resistant due to a marker gene located on the vector.

d. Fermentation

The recombinant preparation of the hCA-ECF2-aa fusion protein is carried out using the microorganisms which contain the hCA-ECF2-aa DNA fragment and/or the vector plasmids (containing hCA-ECF2-aa fragment). The process may be carried out by methods which are known per se, for example, by the method described in WO 92/01707. In accordance with this, commercially available growth media, such as Luria broth, can be used. The fermentations are batch fed with oxygen and amino acid supplementation to provide high cell densities. After the fermentation is complete, the microorganisms may be disrupted as described in WO 92/01707 and the hCA-ECF2-aa fusion protein purified, e.g., using sulfanilamide affinity chromatography as described in WO 92/01707.

II. Cleavage of the Fusion Protein to Yield ECF2-Ala

A fusion protein having the sequence shown below may be cleaved between the amino acids Asn 7 (amino acid 7 of the linker sequence) and Gly $A_{10}$ (amino acid 1 of ECF2-Ala) as indicated by the "*" below.

Specific cleavage at this site can be achieved by treatment with hydroxylamine. The resulting ECF2-Ala fragment (SEQ ID NO:23) may be purified by conventional procedures.

III. Amidation of ECF2-aa (SEQ ID NO:22) to Form ECF2-amide (SEQ ID NO:6)

The amidation of ECF2-aa (SEQ ID NO:22) may be carried out in accordance with WO 92/05271, by transamidating an ECF2-aa peptide such as ECF2-Ala (SEQ ID NO:23) with a nucleophilic amino compound in the presence of carboxypeptidase Y (see Scheme 1 below) to form a peptide intermediate capable of being reacted or decomposed to form ECF2-NH$_2$ (SEQ ID NO:6). Examples of suitable nucleophiles include o-nitrobenzylamines, such as o-nitrophenylglycine amide ("ONPGA"). The transamidation results in a replacement of the C-terminal -aa residue of ECF2-aa (SEQ ID NO:22) by the nucleophilic amine. Photolysis of the resulting photolabile intermediate, e.g., ECF2-ONPGA (SEQ ID NO:28), leads to cleavage of the nucleophile and the production of an ECF2 fragment having an amidated proline at the carboxy terminus ("ECF2-amide"; SEQ ID NO:6). The ECF2-amide may be purified by conventional methods.

SCHEME 1

ECF2-aa  +  ONPGA  $\xrightarrow{\text{CPD-Y}}$  ECF2-ONPGA
(SEQ ID NO:22)                                                    (SEQ ID NO:28)

$\downarrow$ light

ECF2-amide
(SEQ ID NO:6)

IV. Condensation of Elcatonin-Fragment 1 (ECF1) and ECF2-Amide

The N-terminal Elcatonin fragment ECF1 (SEQ ID NO:7) and the Elcatonin related fragment ECF2-Xxx (SEQ ID NO:1) may be coupled using standard peptide coupling reactions as described herein, e.g., in the presence of DCC/HOSu, EDAPC/HOSu or DCC/HOBt. If the coupling reaction is carried out using unprotected forms of ECF1 and ECF2-amide, the C-terminal α-carboxylic acid of the ECF1 fragment is typically converted into an activated ester prior to the addition of the ECF2 fragment. The Elcatonin (SEQ ID NO:13) produced by the coupling reaction may be purified by conventional techniques, such as preparative HPLC methods.

Carba-analogs of other calcitonins (e.g. salmon I calcitonin (SEQ ID NO:38)) and related calcitonin carba analogs may be prepared in a similar manner using ECF1 (SEQ NO:7) and other 10-32 fragments, e.g., the salmon I calcitonin 10-32 fragment (SEQ ID NO:29). The present invention also allows the preparation of carba analogs through the combination of the C-terminal fragment of a calcitonin from one species with an N-terminal carba fragment corresponding to a calcitonin from a different species.

SCHEME 2

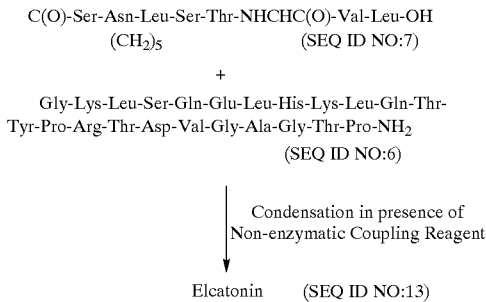

Elcatonin    (SEQ ID NO:13)

V. Cleavage of the Fusion Protein hCA-ECF2-aa to Give the Minifusion Protein (MFP).

In another embodiment of the invention which employs a chemical coupling reaction in the formation of Elcatonin (SEQ ID NO:13), the Met-hCAII'-Met$_{240}$-Val$_{241}$-hCAII"-Linker-ECF2-Ala fusion protein (SEQ ID NO:12) may be cleaved between the Met$_{240}$ and Val$_{241}$ residues via CNBr treatment to yield a 48 amino acid minifusion protein (Val$_{241}$-hCAII"-Linker-ECF2-Ala, hereinafter "MFP" (SEQ ID NO:24)). The MFP is composed of 3 constituent fragments. The amino terminal portion of the minifusion protein essentially constitutes a 24 residue "biological blocking group" on the N-terminus of the ECF2-Ala fragment (SEQ ID NO:23). The MFP (SEQ ID NO:24) may be purified by conventional procedures and subsequently derivatized to protect amino acid side chain residues.

VI. Introduction of Protective Groups into a Minifusion Protein.

When ECF2-aa (SEQ ID NO:22) is to be isolated in a chemically blocked form, a minifusion protein may be separated from the fusion protein following cleavage, and then subjected to chemical derivatization to block

IX. Conversion of Elcatonin-Ala to Elcatonin

The conversion of an amino acid extended Elcatonin precursor to Elcatonin of the formula:

(SEQ ID NO: 13)

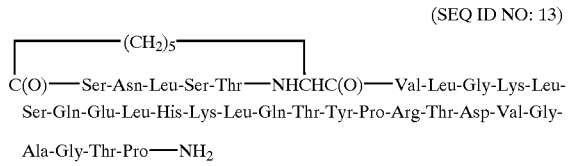

may be affected, in accordance with WO 92/05271, by reacting a precursor polypeptide, Elcatonin-aa (SEQ ID NO:30) with a nucleophilic compound (e.g., ONPGA) in the presence of a carboxypeptidase to give a cleavable intermediate, which may then be cleaved by photolysis to give Elcatonin (which exists as a C-terminal α-carboxamide).

The abbreviations used herein for the amino acids are: Gly, glycine; Lys, L-lysine; Leu, L-leucine; Ser, L-Serine; Gin, L-glutamine; Glu, L-glutamic acid; His, L-histidine; Thr, L-threonine; Tyr, L-tyrosine; Pro, L-proline; Arg, L-arginine; Asp, L-aspartic acid; Val, L-valine; Ala, L-alanine; Met, L-methionine; Asn, L-asparagine; Trp, L-tryptophan; Ile, L-isoleucine; and Phe, L-phenylalanine.

EXAMPLES 1.1 Preparation of the Plasmid pTBN26 Containing DNA Encoding the hCA-ECF2-Ala Fusion Protein A gene encoding amino acids 10-32 of ECF2 was constructed using PCR methodology. The following five oligonucleotides were synthesized at the University of Florida:

```
1. 5' GGA TCC AAG CTT GTT A 3'                                              (SEQ ID NO:32)

2. 5' GTC GAC GAA TTC GAT A 3'                                              (SEQ ID NO:33)

3. 5' GGA TCC AAG CTT GTT AAC GGT AAA CTG TCT CAG GAG CTC CAT AAA CTG 3'    (SEQ ID NO:34)

4. 5' CTG ACG TTG GTG CTG GTA CCC CGG CTT AAG ATA TCG AAT TCG TCG AC 3'     (SEQ ID NO:35)

5. 5' GGT ACC AGC ACC AAC GTC AGT ACG CGG GTA AGT CTG CAG TTT ATG GAG CTC   (SEQ ID NO:36)
      CTG AGA 3'
```

Figure 4A:
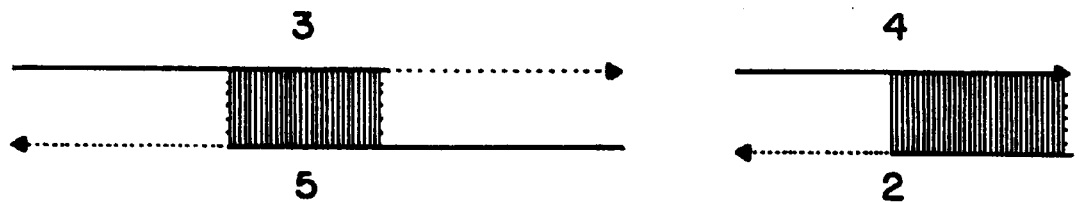
FIG. 4A is a schematic illustration of the first step of the preparation using PCR methodology of a nucleotide sequence encoding ECF2-Ala and additional restriction sites to permit cloning the fragment into plasmids. This step was carried out by conducting a PCR reaction using Taq DNA polymerase on PCR MIX 1.

Oligonucleotides 2-5 were combined in one PCR reaction mixture, PCR MIX 1. The 3' end of oligonucleotide 3 is complementary to the 3' end of oligonucleotide 5, while oligonucleotide 2 is complementary to the 3' end of oligonucleotide 4. These four nucleotides annealed together as shown in FIG. 4A. During PCR, Taq DNA polymerase was used to extend oligonucleotide 3 to the 5' end of oligonucleotide 5, oligonucleotide 5 was extended to the 5' end of oligonucleotide 3, and oligonucleotide 2 was extended to the 5' end of oligonucleotide 4, as indicated by the dotted lines in diagram A.

Figure 4B:
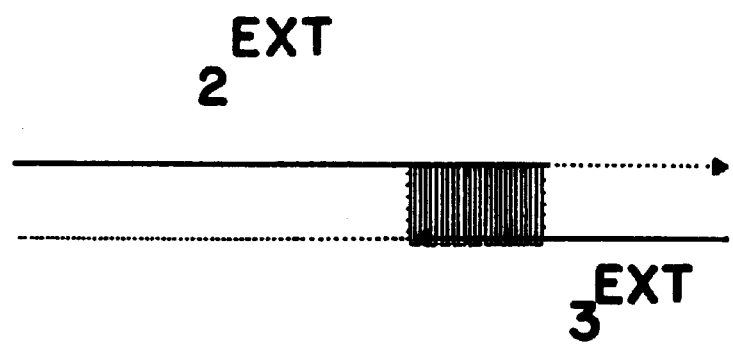
FIG. 4B is a schematic illustration of the second step of the preparation of a DNA sequence encoding ECF2-Ala. The PCR produces derived from the extension of oligonucleotides 2 and 3 in PCR MIX 1 ($2^{Ext}$ (SEQ ID NO:8) and $3^{Ext}$ (SEQ ID NO:9) respectively) have 20 bp of complementary sequence at their 3' ends. The second PCR reaction using Taq DNA polymerase creates a double stranded nucleotide fragment which includes a full length non-interrupted gene sequence encoding ECF2-Ala (SEQ ID NO:10).

A second PCR reaction was used to join the PCR products from PCR MIX 1 resulting in a double stranded nucleotide fragment (SEQ ID NO:10) containing the complete, non-interrupted Asn-ECF2-Ala gene sequence as well as restriction sites to facilitate cloning. The PCR extended products derived from oligonucleotides 2 ($2^{Ext}$ (SEQ ID NO:8) and $3^{Ext}$ respectively (SEQ ID NO:9)) have 20 bp of complementary sequence at their 3' ends (see schematic illustration in FIG. 4B). During the first few cycles of the reaction with PCR MIX 2, oligonucleotides $2^{Ext}$ (SEQ ID NO:8) and $3^{Ext}$ (SEQ ID NO:9) annealed where their sequences were complementary and extended to create the double stranded fragment including the full length non-interrupted gene sequence for ECF2 (SEQ ID NO:10). Finally, oligonucleotides 1 and 2 were used to amplify the full length gene sequence. FIGS. 11 and 12 show the nucleic acid sequences for the complete, non-interrupted ECF2 gene sequence (SEQ ID NO:10) and for oligonucleotides $2^{Ext}$ (SEQ ID NO:8) and $3^{Ext}$ (SEQ ID NO:9) respectively.

Figure 5:
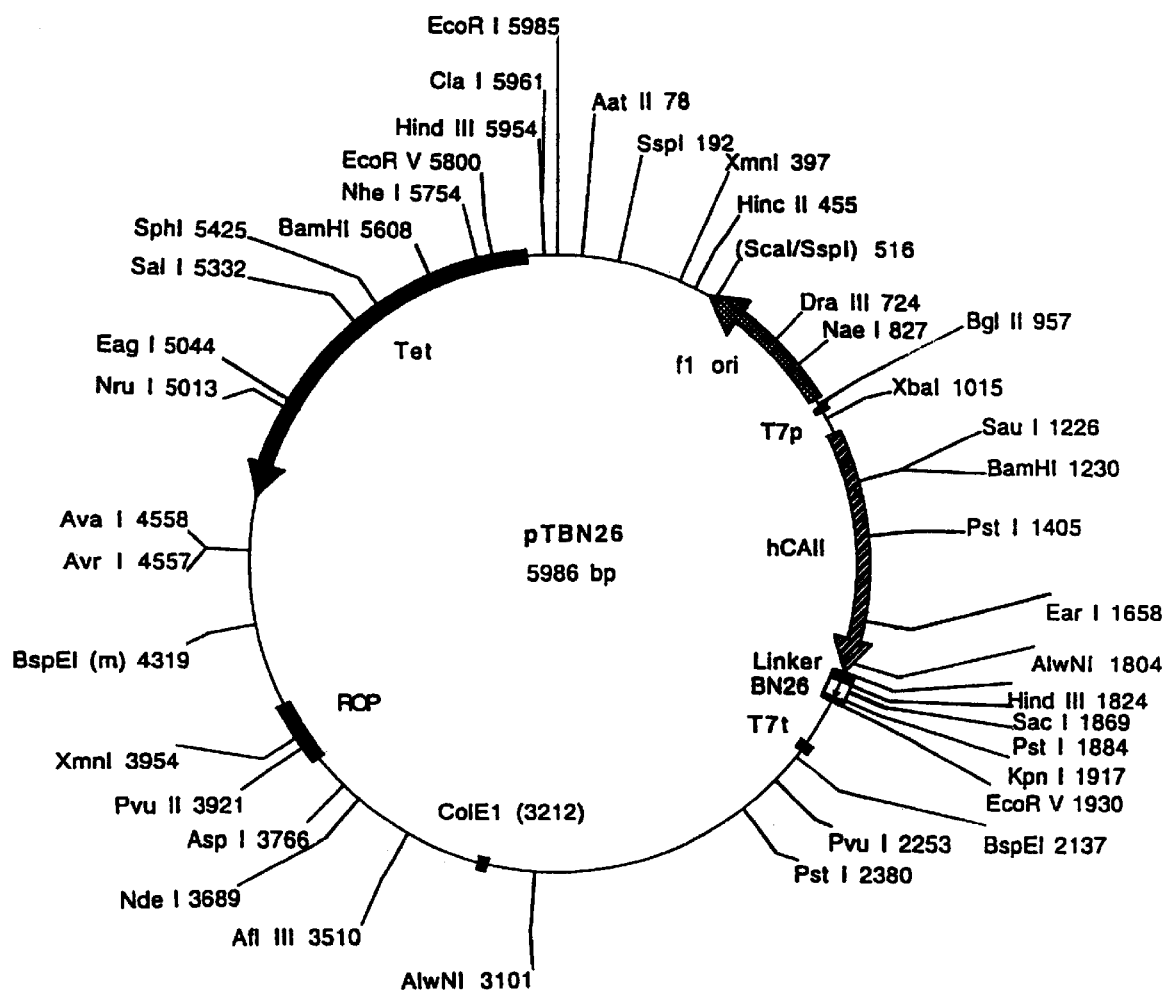
FIG. 5 shows a map of plasmid pTBN26. Plasmid pTBN26 includes a gene sequence for the entire hCAII-Linker-ECF2-Ala ("hCA-ECF2-Ala") fusion protein construct.

The amplified PCR produce was digested with Hpa I and EcoR V. This blunt-ended DNA fragment, that codes for the C-terminal amino acid (Asn) of the polypeptide fragment Linker as well as the entire colypeptide fragment ECF2, was inserted into the pABN plasmid at the unique EcoR V site. The plasmids were screened to insure the Asn-ECF2 gene was inserted in the correct orientation. The resultant plasmid was designated pABN26. Finally, pABN26 was digested with Xba I and BspE I and the entire Met-hCAII'-Met$_{240}$-Val$_{241}$-hCAII"-Linker-ECF2-aa sequence was transferred to pTBN plasmid that had been digested with the same enzymes to create production plasmid pTBN26 (FIG. 5).

The DNA sequence of the final construct with the Met cyanogen bromide cleavage site underlined and the Asn-Gly (SEQ ID NO:11) and corresponding amino acid sequence (SEQ ID NO:12) cleavage site indicated by the arrow is shown in FIG. 6.

1.2 Transformation of the Plasmid pTBN26 (Vector Containing the hCA-ECF2-aa DNA Fragment)

The transformation was carried out in accordance with the procedures described in WO 92/01707. The host microorganisms used were E. coli HB 101 and E. coli BL21(DE3), both being described in van Heeke et al., Protein Expression and Purification, 4, 265-275, (1993).

1.3 Selection of the Vectors Containing hCA-ECF2-Ala DNA

The selection was carried out using standard procedures such as those described in WO 92/01707. The selection was based on the introduction of tetracycline resistance into the host organism.

2. Fermentation of E. coli Containing Plasmid pTBN26

2.1 Growth of a Preculture for Inoculating the Fermentor

The E. coli strain BL21(DE3) containing plasmid pTBN26 was grown in Luria broth (LB) medium containing tetracycline (15 mg/L) and glucose solution (50 mg/L) in a shaking flask at 37° C. untill an optical density at 550 nm (OD550) of about 4 had been reached, about 14 hours. The composition of the Luria broth medium (LB medium) is: 1.0 g/L Tryptone, 1.0 g/L NaCl and 0.5 /L yeast extract.

2.2 Fermentation

Fermentation was performed in a New Brunswick MPP-80 fermentor. The fermentation media, containing 300 g yeast extract, 30 g NaCl and 1200 g casamino acids dissolved in 15 L of $H_2O$, was added to the fermentor followed by 30 L of distilled water. The fermentor was sterilized in place at 121° C. for 25 minutes. After the contents of the fermentor had cooled to 37° C., the following sterile solutions were added sequentially: 480 g glucose in 800 mL $H_2O$, 120 g $MgSO_4.H_2O$ in 250 mL $H_2O$, 495 g $K_2PO_4$ and 465 g $KH_2PO_4$ in 3.0 L of $H_2O$, and 0.9 g tetracycline hydrochloride in a mixture of 30 mL of 95% EtOH and 20 mL $H_2O$. Also, a sterile mineral mix containing 3.6 g $FeSO_4.7\ H_2O$, 3.6 g $CaCl_2.2\ H_2O$, 0.90 g $MnSO_4$, 0.90 g $AlCl_3.6\ H_2O$, 0.09 g $CuCl_2.2\ H_2O$, 0.18 g molybdic acid, and 0.36 g $COCl_2.6\ H_2O$ dissolved in 490.0 mL $H_2O$ and 10.0 mL concentrated HCl was added.

Reagent grade $NH_4OH$ (28%) was attached to the automatic pH feed pump of the fermentor and the pH was adjusted to 6.8. The pH of the fermentation liquid was monitored continuously using a calibrated electrode and maintained at pH 6.8 by the intermittent addition of $NH_4OH$. Additionally, dissolved oxygen was monitored continuously using a calibrated oxygen monitor. Oxygen concentration was maintained by adjusting the stirring rate. Aeration was maintained at 40 L/min. When all systems were operating normally, inoculation was performed by adding 600 mL of inoculum by sterile procedures.

Turbidity, dissolved oxygen, and glucose levels were monitored throughout fermentation. When the turbidity reached an OD(550) of 15 to 20, the medium was supplemented with 300 g of yeast extract and 1,200 g of casamino acids. When the agitation rate reached 500 rpm, pure oxygen was supplemented into the air feed at a rate of 5 L/min and the aeration rate was reduced to 20 L/min to maintain dissolved oxygen at 40%.

When the turbidity reached 30 $OD_{550}$ units, the fermentation medium was rendered 2 mM with respect to isopropylthiolgalactoside to induce the expression of the plasmid. In addition, enough $ZnCl_2$ was added to render the final concentration 100 μM, and a sterile amino acid solution containing 225 g of L-Ser and 75 g each of L-Tyr, L-Trp, L-Phe, L-Pro, and L-His was added to the medium. Two hours after induction, cell samples were removed for analysis. Dry weights and SDS-PAGE protein analysis were performed on samples taken at induction and every 30 minutes thereafter.

At the end of the fermentation, the medium was transferred under sterile conditions to a sterile holding tank and cooled to 8° C. The spent medium was separated from the cells by crossflow filtration using a Millipore Pro Stack equipped with a 200 kD molecular weight cut-off membrane. The cells were concentrated to 5 L, then either processed immediately or packaged in 1 L aliquots in plastic freezer bags and stored at −20° C. for later processing.

Concentrated cells (5 L) were diluted in 32 L of lysis buffer (50 mM Tris, 1 mM EDTA, 0.5% Triton-X100, pH 7.8, containing 0.05 mM phenylmethanesulfonyl fluoride) and then passed two times through a Gaulin APV pilot scale homogenizer operated at 12,000 psi at 4-15° C. The solution was then made 1.3 μM with respect to lysozyme, incubated for 15 minutes (4-15° C.) then passed through a homogenizer a second time.

Approximately 50% of the soluble *E. coli* protein represents hCA-ECF2-aa, assessed by measuring the enzymatic activity of the human carbonic anhydrase portion of the fusion protein in accordance with Verpoorte et al., J. Biol. Chem. 242, 4221-4229, 1967.

2.3 Purification of the hCA-ECF2-Ala Fusion Protein

The lysate (32 L) obtained from Example 2.2 was diluted 1:1 with the lysis buffer without added phenylmethanesulfonyl fluoride and polyethylenimine was added to a final concentration of 0.35%. The whole was stirred for 20 min. and then centrifuged at 10,000×g to remove precipitated DNA, RNA, nonessential proteins, and membrane vesicles and then filtered using a Pall Profile Filter (1.0 μm).

The soluble fusion protein was subsequently purified by affinity chromatography. The pH of the filtered protein solution was adjusted to 8.7 by adding Tris base and loaded onto a 1 L column of p-aminomethylbenzenesulphonamide affinity resin (van Heeke et al., *Methods. Molec. Biol.*, 36, 245-260, 1994) at a flow rate of 200 mL/min. After loading, the column was washed with 5 column volumes of 0.1 M Tris-sulphate buffer pH 9.0, containing 0.2 M $K_2SO_4$ and 0.5 mM EDTA. The resin was then washed with 5 column volumes of 0.1 M Tris-sulphate buffer, pH 7.0, containing 1 M NaCl. The recombinantly produced hCA~ECF2-Ala fusion protein was eluted from the affinity material with 5 column volumes of 0.1 M Tris-sulphate buffer, pH 6.8, containing 0.4 mM potassium thiocyanate and 0.5 mM EDTA. Fractions containing the hCA~ECF2-Ala fusion protein were combined and treated with acetic acid to pH 4.0 to precipitate the product, which was subsequently collected by centrifugation. The resulting paste was frozen and lyophilized The yield for this step was 85%.

3. Cleavage of the hCA-ECF2-Ala Fusion Protein to Give ECF2-Ala 3.1 Cleavage to the hCA-ECF2-Ala Fusion Protein Using Hydroxylamine The fusion protein was cleaved with hydroxylamine between Asn and Gly into an hCAII-containing fragment and the polypeptide fragment ECF2-Ala (SEQ ID NO:23). Cleavage was achieved by incubating 40 g of hCA-ECF2-Ala dissolved in 1 L of hydroxylamine buffer (2 M hydroxylamine hydrochloride, 5 M guanidine hydrochloride, 50 mM 3-(cyclohexylamino) -2-hydroxy-1-propanesulphonic acid, adjusted to pH 10 with lithium hydroxide) for 4 h. An aliquot was removed every hour, and the extent to which the fusion protein has been cleaved to ECF2-Ala was determined by HPLC analysis (C18 Vydac, 4.6×300 mm), buffer A: 0.1% trifluoroacetic acid, 5% acetonitrile by volume, 95% by volume water; buffer B: 0.1% trifluoroacetic acid, 5% by volume water; 95% by volume acetonitrile; linear gradient of 5% buffer A to 68% buffer B; flow rate: 1 mL/min). The reaction was then diluted to 4 L with 15% acetic acid whereupon the resultant precipitated hCAII-containing fragment was removed by centrifugation at 10000×G.

The resulting supernatant from the centrifugation containing ECF2-Ala (SEQ ID NO:23) was then desalted by loading onto a preparative C8 column (5×5.1 cm) equilibrated with 10 mM acetic acid in 5% acetonitrile at a flow rate of 50 mL/min. Following loading, the column was washed with 10 mM acetic acid in 10% acetonitrile, and the ECF2-Ala eluted with 10 mM acetic acid in 45% acetonitrile. The fractions containing ECF2-Ala, identified by analytical HPLC as above, were pooled and lyophilized. In all 1.14 g of ECF2-Ala (SEQ ID NO:23) was obtained, corresponding to a yield of 82%.

3.2 Purification of ECF2-Ala

For the further purification of ECF2-Ala (SEQ ID NO:23), a semipreparative polysulphoethylaspartamide HPLC was used as described in detail in Section 5.3 with a yield of 85%.

4. Conversion of ECF2-Ala to ECF2-Amide

The amidation of ECF2-Ala (SEQ ID NO:23) was carried out according to procedures described in WO 92/05271. ECF2-Ala (12.8 mg) was dissolved in 1 mL of 5 mM EDTA, 25 mM morpholinoethane-sulfonic acid, pH 7.0, and to this was added 72 mg of o-nitrophenylglycine amide (ONPGA). The pH was adjusted to 6.0 with 5 M NaOH and carboxypeptidase-Y (120 μg) was added. After stirring in the dark for about 48 h, acetonitrile (1 mL) was added and the ECF2-ONPGA (SEQ ID NO:28) product purified by C18 reverse phase HPLC as in section 5.2 and the product lyophilized. The course of the amidation reaction was followed by extracting samples for analysis after 10, 60, 120 and 180 min by analytical C18 HPLC as in WO 92/05271.

For the subsequent photolysis, the freezed-dried ECF2-ONPGA (12 mg) was dissolved in 5 mL 50% ethanol. To this solution was added NaHSO$_3$ (26 mg) and sodium benzoate (7.2 mg) and the pH adjusted to 9.5 with 5 M NaOH. Nitrogen was then passed through the reaction mixture for 15 min. The subsequent photolysis, analysis of the course of the reaction, and identification of the resulting ECF2-amide (SEQ ID NO:6), were carried out in accordance with the procedures described in WO 92/05271.

5. Cleavage of the hCA-ECF2-Ala Fusion Protein to Produce the Minifusion Protein

5.1 Chemical Cleavage of the hCA-ECF2-Ala Fusion Protein Using Cyanogen Bromide When chemical rather than enzymatic fragment coupling was employed, the MFP (SEQ ID NO:24) was first cleaved from the fusion protein (SEQ ID NO:12). To cleave the Met$_{240}$-Val$_{241}$ linkage (24 amino acids in the sequence prior to the beginning of ECF2-Ala), 40 mg/mL of the hCA-ECF2-Ala fusion protein (SEQ ID NO:12) was treated with 0.02 M cyanogen bromide in 70% formic acid at room temperature for 6 h under an argon atmosphere in the dark. Methionine (0.03 M) was then added to a final concentration of 0.03 M to terminate the cleavage reaction and the resulting solution was stirred for 30 min. Twice the reaction volume of a solution containing 10% acetic acid and 112 g/L of sodium sulphate was added to the reaction mixture to precipitate the hCAII"-containing fragment and the mixture was stirred for 20 min. The precipitated material was removed by centrifugation (10 min at 10,000×G). The minifusion protein (SEQ ID NO:24) remained soluble in the supernatant. A 58% recovery of MFP (SEQ ID NO:24) in relation to hCA-ECF2-Ala fusion protein (SEQ ID NO:12, employed, was obtained.

5.2 Desalting the Minifusion Protein

The supernatant from the acid precipitation (4.5 g of mini fusion protein) was loaded onto a C8 Vydac semi-preparative column (22×250 mm), which had been equilibrated in 0.1% trifluoracetic acid and 5% acetonitrile. The protein was eluted using 0.1% trifluoracetic acid in 25% acetonitrile, and subsequently lyophilized. In all, 4.05 g of 85% pure mini fusion protein was obtained, corresponding to a yield of 90%.

Figures 7, 8:
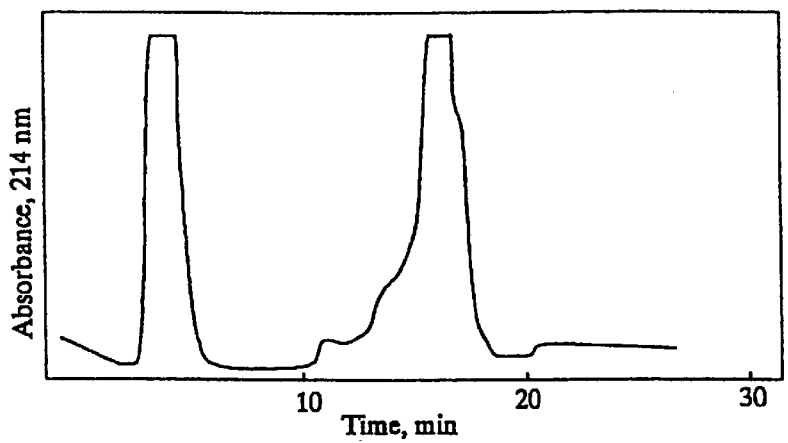
FIG. 7 shows a nucleotide sequence (SEQ ID NO:5) and the amino acid (SEQ ID NO:6) sequence for the 23 amino acid C-terminal fragment ("ECF2") of Elcatonin and eel calcitonin. The nucleotide sequence shown is the sequence encoding ECF2 present in the gene for the hCA-ECF2-Ala fusion protein incorporated into plasmid pTBN26.
FIG. 8 shows a representative preparative HPLC trace (using a polysulfolethyl-aspartamide column) of a sample containing ECF2-amide (SEQ ID NO:6). The peak for ECF2-amide appears between 14.5 and 16.3 minutes.

5.3 Purification of the Minifusion Protein Using Polysulphoethylaspartamide HPLC Polysulphoethylaspartamide chromatography was used for purification of the minifusion protein (SEQ ID NO:24), ECF2-Ala (SEQ ID NO:23) and ECF2-amide (SEQ ID NO:6). The peptide was taken up in buffer A (25 mM acetic acid, 35% acetonitrile) such that the final concentration was 5 mg/mL and then loaded onto a polysulphoethylaspartamide HPLC column (2.2×25 cm) at a flow rate of 20 mL/min. It was subsequently possible to elute the protein, over a period of 30 min, using a linear gradient of 10% buffer B (25 mM acetic acid, 400 mM sodium acetate, 35% acetonitrile) to 47% buffer B. Yields typically were 50% or greater. FIG. 8 shows a representative HLPC trace of a sample containing ECF2-amide (SEQ ID NO:6). The peak for ECF2-amide appears between 14.5 and 16.3 min.

5.4 Desalting Following Polysulphoethylaspartamide HPLC

Following lyophilization, the protein was loaded, for desalting, onto a C8 column (5×20 cm, equilibrated with 95% ethanol). The column was then washed with 4 column volumes of water and with 4 column volumes of 5% ethanol containing 1% acetic acid. The peptide was then eluted with 2 column volumes of 90% ethanol. The fractions were analyzed by HPLC. Yields typically were 80% or greater.

6. Incorporation of Protective Groups into the Minifusion Protein

General Strategy:

The α-amino group of the ECF2 fragment (SEQ ID NO:6) within the recombinant MFP (SEQ ID NO:24) is biologically protected, i.e. protected by the presence of the N-terminal hCAII" fragment. The ε-amino groups of the Lys groups in MFP were protected with acyl donors, such as Z, BOC, ADOC or FMOC. The reaction of the arginine-guanido function with Z-OSU was prevented by salt formation with HCl. The reaction of the His nitrogen with Z-OSU was suppressed by adding agents such as N-hydroxysuccinimide.

Experimental Procedure

MFP (SEQ ID NO:24) (270 mg) was dissolved in water (20 mL), and dioxane (4 mL) and 680 μL of 0.1 N HCl (to ensure salt formation at the two arginine-guanidino functions) was added. Prior to reaction, 78 mg of N-hydroxysuccinimide and 104.7 μL of triethylamine were added to protect the His nitrogen, and either 169 mg of Z-OSU, 146 mg of BOC-OSU, 135 mg of ADOC fluoride or 229 mg of FMOC-OSU were then added to the whole, with cooling.

The reaction mixture was then stirred at room temperature for 24 h and subsequently dried in vacuo. The resulting residue was carefully triturated with dichloromethane (twice) and then with acetonitrile (twice). The product was collected by filtration and dried in vacuo. The yields of the Z protected mini fusion protein was 300 mg and of BOC-protected protein 295 mg, and that of ADOC-protected and FMOC-protected protein was 310 mg.

Checking for complete reaction of mini fusion protein with the respective protective groups was carried out by means of thin layer chromatography using protected and unprotected peptides. Complete reaction was verified on thin layer silica plates (eluent: phenol:H2O, 775:225). The yield for the Z-OSU reaction when 540 mg of MFP (SEQ ID NO:24) was used was 75% and was typical of that found for the other blocking agents.

7. Cleavage of a Protected Mini Fusion Protein to Produce a Protected ECF2-Ala Fragment

7.1 Cleavage Using Hydroxylamine

In order to liberate the α-amino group which was biologically protected by amino acid sequence, the protected mini fusion protein was cleaved with hydroxylamine between Asn and Gly into a Z-protected ECF2-Ala fragment (SEQ ID NO:23) and the 24 amino acid-long Trp-containing fragment. The composition of the hydroxylamine buffer was the same as in Section 3.1.

Hydroxylamine buffer (26 mL) was added to 260 mg of Z-protected minifusion protein (SEQ ID NO:24), and the whole was then ultrasonicated (20 sec) and the pH adjusted to pH 10.0 with 4 M lithium hydroxide. The resulting mixture was incubated at 30° C. and pH 10.0 for up to 5 h. The pH was then adjusted to 6.0 using concentrated acetic acid.

An aliquot was removed every hour, and the extent to which the Z-protected minifusion protein (SEQ ID NO:24)

has been cleaved to the Z-protected ECF2-Ala fragment (SEQ ID NO:23) was determined by HPLC analysis (C18 Vydac column, 5×300 mm), buffer A: 0.1% trifluoroacetic acid; buffer B 0.1% trifluoroacetic acid, 5% by volume H2O, 95% acetonitrile; eluent: linear gradient of 5% buffer A to 68% buffer B; 1 mL/min). Termination of the hydroxylamine cleavage was as in 3.1.

Fractions obtained from the C8 column were analyzed by HPLC using a Vydac C18 column. The buffers for the HPLC were those previously described. The flow rate was 1 mL/min. The proteins were eluted by a linear gradient from 41% buffer A to 71% buffer B. Detection was at 210 nm. In all, 156 mg of Z-protected ECF2-Ala ("Z-ECF2-Ala" (SEQ ID NO:23)) were obtained, corresponding to a yield of 60%.

7.2 Purification of Z-ECF2-Ala

Z-ECF2-Ala (SEQ ID NO:23) was purified by use of a semi-preparative C8 HPLC. Z-ECF2-Ala (160 mg) was dissolved in 5 M acetic acid (5 mL), and buffer A (100 mM acetic acid, 5% acetonitrile (5 mL) was subsequently added. The sample was then loaded onto a semi-preparative HPLC C8 column (details as in 3.2.). Following the hydroxylamine cleavage and the purification, 120 mg of Z-ECF2-Ala (SEQ ID NO:23) was obtained, corresponding to a yield of 75% for the C8 purification step.

For the further purification of Z-ECF2-Ala (SEQ ID NO:23), a semi-preparative polysulphoethylaspartamide HPLC was used as described in Section 5.3 below. Using this method, 59 mg of 95-98% pure Z-ECF2-Ala was obtained, corresponding to a yield of 85.5%.

8. Condensation of ECF2-amide and ECF1-OMe

Amidated ECF2 (SEQ ID NO:6) produced according to Example 4 and the cyclic Elcatonin-fragment ECF1 (SEQ ID NO:3) may be coupled in the presence of a non-enzymatic coupling reagent. For example, dicyclohexylcarbodiimide (DCC) and N-hydroxysuccinimide (HOSu) may be added to a solution of ECF1 (SEQ ID NO:3) having the side hydroxyl groups of Ser and Thr protected as a benzyl ether and ECF2-amide (SEQ ID NO:2) having the reactive side chain groups of Lys, Ser, Thr and/or Glu residues protected. The reaction is stirred at about 0° C. for 8 hours. Fragment condensation during this time was followed by HPLC analysis. After termination of the reaction, the mixture may be diluted by adding 1% trifluoracetic acid. The product Elcatonin (SEQ ID NO:13) may be purified by preparative HPLC. Unreacted ECF2-amide (SEQ ID NO:2) may be isolated and purified by HPLC and recycled.

9. Chemical Coupling of Z-ECF2 to ECF1

The coupling of the free α-amino group of the Z-ECF2-Ala fragment (i.e., EFC2-Ala having the side chain amino groups protected with a carbobenzyloxy group) to the free C-terminal α-carboxyl group of the peptide fragment ECF1 may carried out either by the carbodiimide or the azide methods (see, e.g., Greenstein et al., in *Chemistry of the Amino Acids*, Vol. 2, John Wiley, New York, pp 804ff, 1016ff, (1961)). The coupling reaction is typically carried out by adding the Z-ECF2-Ala fragment to an activated ester formed from the C-terminal α-carboxylic acid of the ECF1 fragment. Removal of the Cbz protecting groups from the coupling product may be carried out via hydrogenolysis and the resulting product purified by preparative HPLC to yield Elcatonin-Ala (i.e., "ECF1-ECF2-Ala"; SEQ ID NO:31)

10. Conversion of Elcatonin-Ala to Elcatonin-Amide

The Elcatonin-Ala (SEQ ID NO:31) peptide produced according to Section 9 may be amidated using the procedure described in Section 4. The amidated Elcatonin (SEQ ID NO:13) may be purified and subsequently desalted using the procedures described in Sections 5.3 and 5.4.

The invention has been described with reference to various specific and preferred embodiments and techniques. However, it should be understood that many variations and modifications may be made while remaining within the spirit and scope of the invention.

The publications referred to in this specification are indicative of the level of ordinary skill in the art to which this invention pertains and are herein incorporated by reference to the same extent as if each individual publication was specifically and individually indicated by reference.

What is claimed is:

1. An isolated nucleic acid comprising a polynucleotide having the sequence of SEQ ID NO: 11.

2. A recombinant DNA construct comprising a polynucleotide having the sequence of SEQ ID NO: 11.

* * * * *